(12) United States Patent
Arcot-Krishnamurthy et al.

(10) Patent No.: US 8,412,326 B2
(45) Date of Patent: Apr. 2, 2013

(54) PACEMAKER WITH VAGAL SURGE MONITORING AND RESPONSE

(75) Inventors: Shantha Arcot-Krishnamurthy, Vadnais Heights, MN (US); Eric A. Mokelke, White Bear Lake, MN (US); Allan C. Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 391 days.

(21) Appl. No.: 12/709,867

(22) Filed: Feb. 22, 2010

(65) Prior Publication Data
US 2011/0106197 A1 May 5, 2011

Related U.S. Application Data

(60) Provisional application No. 61/256,718, filed on Oct. 30, 2009.

(51) Int. Cl.
*A61N 1/00* (2006.01)
(52) U.S. Cl. .......................................... 607/14
(58) Field of Classification Search .................. 607/9
See application file for complete search history.

(56) References Cited

U.S. PATENT DOCUMENTS

| | | | |
|---|---|---|---|
| 4,587,975 A | 5/1986 | Salo et al. | |
| 4,834,710 A | 5/1989 | Fleck | |
| 4,919,133 A | 4/1990 | Chiang | |
| 5,007,427 A | 4/1991 | Sukuki et al. | |
| 5,072,458 A | 12/1991 | Suzuki | |
| 5,111,818 A | 5/1992 | Suzuki et al. | |
| 5,135,004 A | 8/1992 | Adams et al. | |
| 5,184,615 A | 2/1993 | Nappholz et al. | |
| 5,199,428 A | 4/1993 | Obel et al. | |
| 5,282,840 A | 2/1994 | Hudrlik et al. | |
| 5,313,953 A | 5/1994 | Yomtov et al. | |
| 5,360,436 A | 11/1994 | Alt et al. | |
| 5,376,106 A | 12/1994 | Stahmann et al. | |
| 5,391,188 A | 2/1995 | Nelson et al. | |
| 5,484,419 A | 1/1996 | Fleck | |

(Continued)

FOREIGN PATENT DOCUMENTS

| EP | 0879618 A1 | 11/1998 |
|---|---|---|
| EP | 1437159 A1 | 7/2004 |

(Continued)

OTHER PUBLICATIONS

"U.S. Appl. No. 11/682,448 Final Office Action mailed Oct. 7, 2010", 6 pgs.

(Continued)

*Primary Examiner* — Christopher D Koharski
*Assistant Examiner* — Philip Edwards
(74) *Attorney, Agent, or Firm* — Schwegman Lundberg & Woessner, P.A.

(57) ABSTRACT

A pacemaker initiates and times a monitoring interval in response to an event such as a therapy delivery to a patient. The monitoring interval is specified to include a duration of an anticipated acute response to the event, such as vagal surge. One or more physiological parameters indicative of the acute response are detected during the monitoring interval for analyzing therapeutic effect of the event. In various embodiments, one or more pacing parameters are adjusted for a response interval specified to include the duration of the anticipated acute response to allow for the analysis and maximization of the therapeutic effect. In various embodiments, the event includes a session of pacing therapy delivered according to an intermittent cardiac stress augmentation pacing protocol, and the therapeutic effect is analyzed to adjust that protocol.

40 Claims, 15 Drawing Sheets

U.S. PATENT DOCUMENTS

| | | |
|---|---|---|
| 5,531,768 A | 7/1996 | Alferness |
| 5,588,432 A | 12/1996 | Crowley |
| 5,634,899 A | 6/1997 | Shapland et al. |
| 5,649,968 A | 7/1997 | Alt et al. |
| 5,755,671 A | 5/1998 | Albrecht et al. |
| 5,919,209 A | 7/1999 | Schouten |
| 6,021,350 A | 2/2000 | Mathson |
| 6,108,577 A | 8/2000 | Benser |
| 6,115,628 A | 9/2000 | Stadler et al. |
| 6,233,486 B1 | 5/2001 | Ekwall et al. |
| 6,238,422 B1 | 5/2001 | Oort |
| 6,256,538 B1 | 7/2001 | Ekwall |
| 6,272,379 B1 | 8/2001 | Fischell et al. |
| 6,278,894 B1 | 8/2001 | Salo et al. |
| 6,285,907 B1 | 9/2001 | Kramer et al. |
| 6,314,323 B1 | 11/2001 | Ekwall et al. |
| 6,368,284 B1 | 4/2002 | Bardy |
| 6,445,953 B1 | 9/2002 | Bulkes et al. |
| 6,477,402 B1 | 11/2002 | Lynch et al. |
| 6,501,983 B1 | 12/2002 | Natarajan et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,763,267 B2 | 7/2004 | Ding |
| 6,827,690 B2 | 12/2004 | Bardy |
| 6,838,471 B2 | 1/2005 | Tracey |
| 6,842,642 B2 | 1/2005 | Vanhout |
| 6,845,267 B2 | 1/2005 | Harrison et al. |
| 6,865,420 B1 | 3/2005 | Kroll |
| 6,892,095 B2 | 5/2005 | Salo |
| 6,907,285 B2 | 6/2005 | Denker et al. |
| 6,913,577 B2 | 7/2005 | Bardy |
| 6,937,899 B2 | 8/2005 | Sheldon et al. |
| 6,950,701 B2 | 9/2005 | Begemann et al. |
| 6,965,797 B2 | 11/2005 | Pastore et al. |
| 6,973,349 B2 | 12/2005 | Salo |
| 7,010,345 B2 | 3/2006 | Hill et al. |
| 7,039,462 B2 | 5/2006 | Pastore et al. |
| 7,062,314 B2 | 6/2006 | Zhu et al. |
| 7,062,325 B1 | 6/2006 | Krig et al. |
| 7,069,070 B2 | 6/2006 | Carlson et al. |
| 7,072,711 B2 | 7/2006 | Girouard et al. |
| 7,171,258 B2 | 1/2007 | Goode |
| 7,215,992 B2 | 5/2007 | Stahmann et al. |
| 7,215,997 B2 | 5/2007 | Yu et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,340,303 B2 | 3/2008 | Zhu |
| 7,364,547 B2 | 4/2008 | Stahmann et al. |
| 7,366,568 B2 | 4/2008 | Pastore et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,668,594 B2 | 2/2010 | Marina et al. |
| 2002/0042632 A1 | 4/2002 | Iaizzo et al. |
| 2002/0072777 A1 | 6/2002 | Lu |
| 2002/0082660 A1 | 6/2002 | Stahmann et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0060854 A1 | 3/2003 | Zhu |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0233130 A1 | 12/2003 | Padmanabhan et al. |
| 2004/0015081 A1 | 1/2004 | Kramer et al. |
| 2004/0038947 A1 | 2/2004 | Wink et al. |
| 2004/0049235 A1 | 3/2004 | Deno et al. |
| 2004/0088017 A1 | 5/2004 | Sharma et al. |
| 2004/0102815 A1 | 5/2004 | Balczewski et al. |
| 2004/0106960 A1 | 6/2004 | Siejko et al. |
| 2004/0106961 A1 | 6/2004 | Siejko et al. |
| 2004/0133247 A1 | 7/2004 | Stahmann et al. |
| 2004/0138719 A1 | 7/2004 | Cho et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0075673 A1 | 4/2005 | Warkentin et al. |
| 2005/0090719 A1 | 4/2005 | Scheiner et al. |
| 2005/0096706 A1 | 5/2005 | Salo |
| 2005/0137631 A1 | 6/2005 | Yu et al. |
| 2005/0143779 A1 | 6/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0283195 A1 | 12/2005 | Pastore et al. |
| 2005/0288721 A1 | 12/2005 | Girouard et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0206158 A1 | 9/2006 | Wu et al. |
| 2006/0241357 A1 | 10/2006 | Chirife |
| 2006/0241704 A1 | 10/2006 | Shuros et al. |
| 2006/0247686 A1 | 11/2006 | Girouard et al. |
| 2006/0247700 A1 | 11/2006 | Jackson |
| 2006/0253156 A1 | 11/2006 | Pastore et al. |
| 2006/0259087 A1 | 11/2006 | Baynham et al. |
| 2006/0259088 A1 | 11/2006 | Pastore et al. |
| 2006/0271119 A1 | 11/2006 | Ni et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0150005 A1 | 6/2007 | Sih et al. |
| 2007/0150015 A1 | 6/2007 | Zhang et al. |
| 2007/0162081 A1 | 7/2007 | Yu et al. |
| 2007/0179392 A1 | 8/2007 | Zhang |
| 2007/0239218 A1 | 10/2007 | Carlson et al. |
| 2007/0282380 A1 | 12/2007 | Brooke et al. |
| 2007/0299356 A1 | 12/2007 | Wariar et al. |
| 2008/0027495 A1 | 1/2008 | Prinzen et al. |
| 2008/0058661 A1 | 3/2008 | Bardy |
| 2008/0058881 A1 | 3/2008 | Wagner et al. |
| 2008/0081354 A1 | 4/2008 | Qu et al. |
| 2008/0082135 A1 | 4/2008 | Arcot et al. |
| 2008/0091138 A1 | 4/2008 | Pastore et al. |
| 2008/0132972 A1 | 6/2008 | Shuros et al. |
| 2008/0140141 A1 | 6/2008 | Ben-David et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0215105 A1 | 9/2008 | Pastore et al. |
| 2008/0221636 A1* | 9/2008 | Pastore et al. .................. 607/18 |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0281591 A1 | 11/2009 | Shuros et al. |
| 2010/0016913 A1 | 1/2010 | Arcot-Krishnamurthy et al. |
| 2010/0016916 A1 | 1/2010 | Arcot-Krishnamurthy et al. |
| 2010/0130913 A1 | 5/2010 | Baynham et al. |
| 2011/0071584 A1 | 3/2011 | Mokelke et al. |

FOREIGN PATENT DOCUMENTS

| | | |
|---|---|---|
| EP | 1690566 A1 | 8/2006 |
| WO | WO-9518649 A1 | 7/1995 |
| WO | WO-0078391 A1 | 12/2000 |
| WO | WO-0115609 A1 | 3/2001 |
| WO | WO-2004058326 A2 | 7/2004 |
| WO | WO-2006074189 A1 | 7/2006 |
| WO | WO-2006079010 A1 | 7/2006 |
| WO | WO-2006115693 A2 | 11/2006 |
| WO | WO-2006115693 A3 | 11/2006 |
| WO | WO-2006121842 A2 | 11/2006 |
| WO | WO-2006124636 A2 | 11/2006 |
| WO | WO-2006124729 A2 | 11/2006 |
| WO | WO-2007133962 A2 | 11/2007 |

| WO | WO-2008109040 A2 | 9/2008 |
| WO | WO-2009/114081 A1 | 9/2009 |
| WO | WO-2011/053369 A1 | 5/2011 |

OTHER PUBLICATIONS

"U.S. Appl. No. 11/682,448, Advisory Action mailed Feb. 4, 2011", 5 pgs.

"U.S. Appl. No. 11/682,448, Non Final Office Action mailed Jun. 23, 2011", 8 pgs.

"U.S. Appl. No. 11/682,448, Response filed Feb. 7, 2011 to Final Office Action mailed Oct. 7, 2010", 14 pgs.

"U.S. Appl. No. 11/682,448, Response filed Feb. 7, 2011 to Final Office Action mailed Oct. 7, 2010 and Advisory Action mailed Feb. 4, 2011", 15 pgs.

"U.S. Appl. No. 11/682,448, Response filed Jul. 1, 2010 to Non Final Office Action mailed Apr. 5, 2010", 12 pgs.

"European Application Serial No. 08726356.2, Office Action mailed May 31, 2010", 7 pgs.

"European Application Serial No. 08726356.2, Response filed Aug. 27, 2010 to Communication dated May 31, 2010", 14 pgs.

"International Application Serial No. PCT/US2008/002799, International Search Report mailed Oct. 15, 2008", 6 pgs.

"International Application Serial No. PCT/US2008/002799, Invitation to Pay Fees and Partial International Search Report mailed Jul. 14, 2008", 7 pgs.

"International Application Serial No. PCT/US2008/002799, Written Opinion mailed Oct. 15, 2008", 11 pgs.

Kin, Hajime, et al., "Postconditioning attenuates myocardial ischemia-reperfusion injury by inhibiting events in the early minutes of reperfusion", *Cardiovascular Research*, 62(1), (Apr. 1, 2004), 74-85.

Kis, A., "Repeated cardiac pacing extends the time during which canine hearts are protected against ischaemia-induced arrhythmias : role of nitric oxide.", *Journal of Molecular and Cellular Cardiology*, 31(6), (Jun. 1999), 1229-1241.

Kloner, R. A., et al., "Prospective temporal analysis of the onset of preinfarction angina versus outcome: an ancillary study in TIMI-9B", *Circulation*, 97(11), (1998), 1042-5.

Koning, M M, "Rapid ventricular pacing produces myocardial protection by nonischemic activation of KATP+ channels", *Circulation*, 93(1), (Jan. 1, 1996), 178-186.

Krayenbuhl, H. P., "Hemodynamics in ischemia. Systolic phase", *Z. Kardiol.*, 73 Suppl 2, [Article in German with English Abstract], (1984), 119-25.

Murry, C. E., et al., "Preconditioning with ischemia: a delay of lethal cell injury in ischemic myocardium", *Circulation*, 74(5), (1986), 1124-1136.

Ovize, M., et al., "Stretch preconditions canine myocardium.", *Am J Physiol.*, 266(1 Pt 2), (Jan. 1994), H137-46.

Prinzen, Frits W, "Mapping of regional myocardial strain and work during ventricular pacing: experimental study using magnetic resonance imaging tagging", *Journal of the American College of Cardiology*, 33(6), (May 1999), 1735-1742.

Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.

Tsang, A., et al., "Postconditioning: a form of "modified reperfusion" protects the myocardium by activating the phosphatidylinositol 3-kinase-Akt pathway", *Circ Res.*, 95(3), Epub Jul. 8, 2004, (Aug. 6, 2004), 230-2.

Vanagt, W. Y. R., et al., "Ventricular Pacing for Improving Myocardial Tolerance to Ischemia", *Progress Report on Project Guidant-CARIM*, (Oct. 2003), 1-25.

Vegh, A, et al., "Transient ischaemia induced by rapid cardiac pacing results in myocardial preconditioning", *Cardiovascular Research*, 25(12), (Dec. 1991), 1051-3.

Wu, Zhong-Kai, et al., "Ischemic preconditioning suppresses ventricular tachyarrhythmias after myocardial revascularization", *Circulation*, 106(24), (Dec. 10, 2002), 3091-3096.

Zhao, Zhi-Qing, et al., "Inhibition of myocardial injury by ischemic postconditioning during reperfusion: comparison with ischemic preconditioning", *Am J Physiol Heart Circ Physiol*, 285(2), (Aug. 2003), H579-H588.

"U.S. Appl. No. 11/682,448, Non-Final Office Action mailed Apr. 5, 2010", 16 pgs.

"International Application Serial No. PCT//US2010/024930, International Search Report mailed Jun. 2, 2010", 4 pgs.

"International Application Serial No. PCT//US2010/024930, Written Opinion mailed Jun. 2, 2010", 8 pgs.

"U.S. Appl. No. 11/682,448, Final Office Action mailed Dec. 8, 2011", 10 pgs.

"U.S. Appl. No. 11/682,448, Non Final Office Action mailed Aug. 13, 2012", 9 pgs.

"U.S. Appl. No. 11/682,448, Response filed Mar. 6, 2012 to Final Office Action mailed Dec. 8, 2011", 14 pgs.

"U.S. Appl. No. 11/682,448, Response filed Sep. 23, 2011 to Non Final Office Action mailed Jun. 23, 2011", 13 pgs.

"International Application Serial No. PCT/US2010/024930, International Preliminary Report on Patentability mailed May 10, 2012", 9 pgs.

"Japanese Application Serial No. N/A, Voluntary Amendment filed May 31, 2012", 7 pgs.

\* cited by examiner

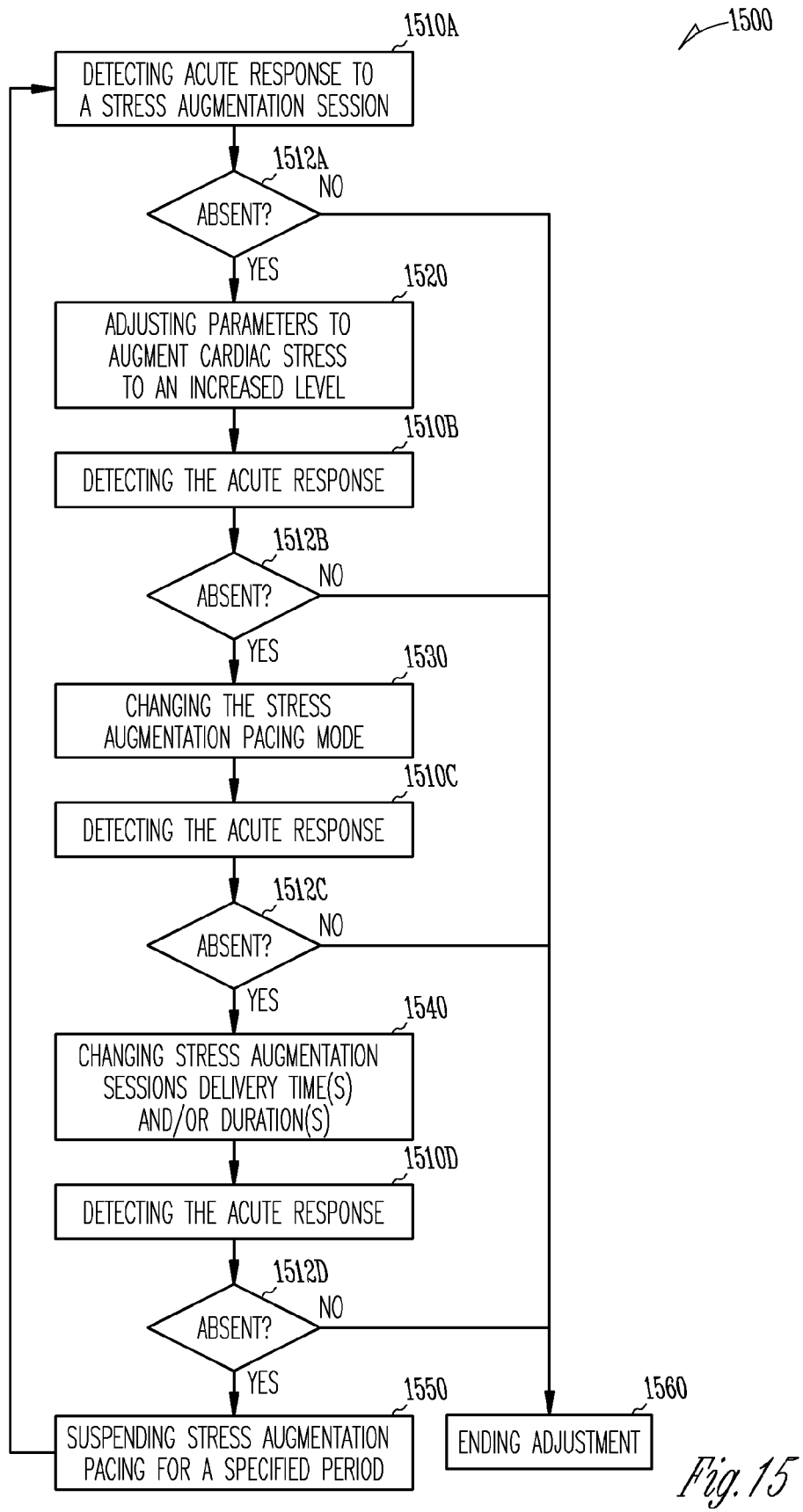

PACEMAKER WITH VAGAL SURGE MONITORING AND RESPONSE

CROSS-REFERENCE TO RELATED APPLICATIONS

This application claims the benefit of U.S. Provisional Application No. 61/256,718, filed on Oct. 30, 2009, under 35 U.S.C. §119(e), which is hereby incorporated by reference.

TECHNICAL FIELD

This document relates generally to cardiac rhythm management (CRM) systems and particularly a pacemaker that provides for monitoring and pacing adjustment following an event associated with anticipated vagal surge.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes irregular contractions of the myocardium, a condition generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms.

Various types of therapies have been developed to treating a patient with heart failure by improving the patient's conditions and quality of life. Examples of such therapies include cardiac pacing, neurostimulation, and drug therapies. Because different types of pacing and/or other therapies may function with different underlying mechanisms, serve different specific purposes, and have different levels of effectiveness in different patients, there is a need to adjust their parameters and coordinate their deliveries to maximize the overall beneficial effects to each patient.

SUMMARY

A pacemaker initiates and times a monitoring interval in response to an event such as a therapy delivery to a patient. The monitoring interval is specified to include a duration of an anticipated acute response to the event, such as vagal surge. One or more physiological parameters indicative of the acute response are detected during the monitoring interval for analyzing therapeutic effect of the event. In various embodiments, one or more pacing parameters are adjusted for a response interval specified to include the duration of the anticipated acute response to allow for the analysis and maximization of the therapeutic effect. In various embodiments, the event includes a session of pacing therapy delivered according to an intermittent cardiac stress augmentation pacing protocol, and the therapeutic effect is analyzed to adjust that protocol.

In one embodiment, a system includes a monitoring circuit, a pacing output circuit, and a pacing control circuit. The monitoring circuit includes a monitoring timer, a sensing circuit, and a detection circuit. The monitoring timer initiates and times a monitoring interval that includes an anticipated duration of vagal surge resulting from a specified type event. The sensing circuit senses one or more physiological signals each indicative of a level of the vagal surge. The one or more physiological signals include at least a cardiac signal. The detection circuit detects one or more parameters each indicative of the level of the vagal surge using the sensed one or more physiological signals. The one or more parameters include at least an intrinsic heart rate. The pacing output circuit delivers pacing pulses. The pacing control circuit controls the delivery of the pacing pulses using pacing parameters and includes a response timer and a parameter adjustment module. The response timer initiates and times a response interval following the specified type event. The response interval includes the anticipated duration of the vagal surge. The parameter adjustment module adjusts one or more pacing parameters of the pacing parameters to allow the heart to beat at the intrinsic heart rate during the response interval.

In one embodiment, a method for operating a pacing system is provided. A cardiac signal is sensed from a patient's heart. Pacing pulses are delivered to the patient's heart. The delivery of the pacing pulses is controlled using pacing parameters. A monitoring interval is initiated in response to a specified type event. The monitoring interval includes an anticipated duration of vagal surge resulting from the specified type event. An intrinsic heart rate is detected from the cardiac signal during the monitoring interval. A response interval is initiated in response to the specified type event. The response interval includes the anticipated duration of the vagal surge. One or more pacing parameters of the pacing parameters are adjusted to allow the heart to beat at the intrinsic heart rate during the response interval.

In one embodiment, a system includes a monitoring circuit, a pacing output circuit, and a pacing control circuit. The monitoring circuit includes a monitoring timer, a sensing circuit, and a detection circuit. The monitoring timer initiates and times a monitoring interval including an anticipated duration of an acute response to a stress augmentation pacing session of a plurality of stress augmentation pacing sessions. The sensing circuit senses one or more physiological signals each indicative of a level of the acute response. The detection circuit detects the acute response using the one or more physiological signals sensed during the monitoring interval and produces an acute response signal after expiration of the monitoring interval. The acute response signal is indicative of a status of the acute response. The pacing output circuit delivers pacing pulses. The pacing control circuit includes a memory circuit, an intermittent cardiac stress augmentation pacing protocol stored in the memory circuit, a pacing protocol execution module, and a stress augmentation pacing adjustment module. The intermittent cardiac stress augmentation pacing protocol specifies the plurality of stress augmentation pacing sessions and a stress augmentation pacing mode including pacing parameters. The pacing parameters are selected to augment cardiac stress to a level effective in slowing or stopping progression of a cardiac disorder. The pacing protocol execution module controls the delivery of the pacing pulses by executing the intermittent cardiac stress augmentation pacing protocol. The stress augmentation pacing adjustment module adjusts the intermittent cardiac stress augmentation pacing protocol using the acute response signal.

In one embodiment, a method for operating a system for pacing a heart is provided. Pacing pulses are delivered to the heart. The delivery of the pacing pulse is controlled by executing an intermittent cardiac stress augmentation pacing protocol. The intermittent cardiac stress augmentation pacing protocol specifies a plurality of stress augmentation pacing sessions and a stress augmentation pacing mode including pacing parameters. The pacing parameters are selected to augment cardiac stress to a level effective in slowing or stopping progression of a cardiac disorder. A monitoring interval is timed. The monitoring interval includes an anticipated duration of an acute response to a stress augmentation pacing session of the plurality of stress augmentation pacing sessions. One or more physiological signals each indicative of a level of the acute response are sensed. The acute response is detected using the one or more physiological signals sensed during the monitoring interval. An acute response signal is produced after expiration of the monitoring interval. The acute response signal is indicative of a status of the acute response for the stress augmentation pacing session. The intermittent cardiac stress augmentation pacing protocol is adjusted using the acute response signal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 15 is a flow chart illustrating an embodiment of a method for adjusting the intermittent cardiac stress augmentation pacing protocol in response to absence of acute response.

DETAILED DESCRIPTION

Figure 1:
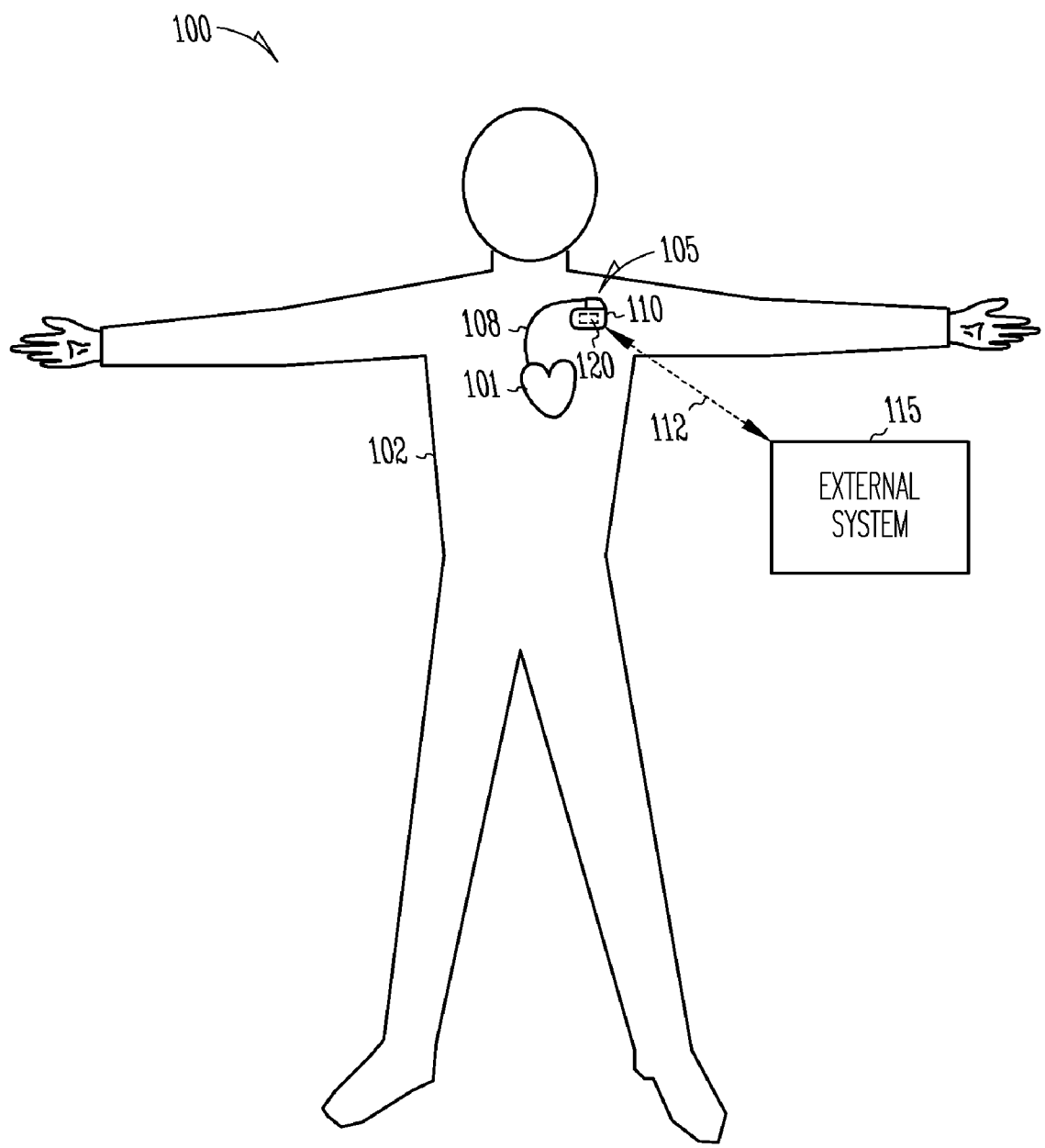
FIG. 1 is an illustration of an embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a CRM system including an implantable medical device that delivers cardiac pacing to a patient and adjusts its monitoring and pacing functions following an event anticipated to cause an acute response including vagal surge in the patient. In various embodiments, the event is a delivery of therapy whose anticipated effects include vagal surge that has therapeutic benefits to the patient.

For example, the implantable medical device is implanted in the patient to provide pacing therapy to improve hemodynamic performance and control progression of the heart failure. A bradycardia or cardiac resynchronization pacing therapy is delivered chronically but paused for sessions of cardiac stress augmentation pacing therapy. The cardiac stress augmentation pacing (also referred to as "stress augmentation pacing" herein) creates or augments regional stress in the patient's heart, such as by selecting pacing parameters to increase the degree of ventricular asynchrony. During each therapy session, the pacing pulses are delivered according to a stress augmentation pacing sequence that includes alternating non-pacing and pacing periods or alternating periods of different pacing modes. The therapy sessions are initiated according to a programmed delivery schedule that may be adjusted dynamically based on the patient's physiological and pathological conditions, daily activities, and other medical treatments. Experiments have shown that a cardiac stress augmentation pacing therapy using intermittent dyssynchronous pacing prevents progressive left ventricular dilatation and hypertrophy in a volume and pressure overload animal model. Experiments have also shown increased fractional area of shortening (FAS) and lowered intrinsic heart rate following a delivery of the cardiac stress augmentation pacing therapy. The FAS is a measure of cardiac contractility. The lowered intrinsic heart rate indicates a vagal surge. Such acute response to the cardiac stress augmentation pacing therapy may last for several hours following each session of the cardiac stress augmentation pacing therapy. In various embodiments, when the delivery of the bradycardia or cardiac resynchronization pacing therapy is resumed following a session of the stress augmentation pacing therapy, the pacing parameters are adjusted if necessary so as not to suppress the acute response including the vagal surge by letting the patient's heart beat at its intrinsic rate. In various embodiments, the acute response is monitored and analyzed to adjust the stress augmentation pacing therapy for its subsequent sessions.

Another example of the event anticipated to cause vagal surge in the patient potentially includes certain types of neurostimulation for modulating cardiovascular functions. More generally, the event anticipated to cause vagal surge may potentially include any drug delivery, exercise, or other events associated with vagal surge. In various embodiments, the implantable medical device monitors the vagal surge and adjusts its pacing therapy during the anticipated duration of the vagal surge for analyzing and maximizing the therapeutic benefit to the patient. In various embodiments, the implantable medical device adjusts one or more therapies that cause the acute responses including the vagal surge using the analysis of the therapeutic benefit.

FIG. 1 is an illustration of an embodiment of a CRM system 100 and portions of an environment in which system 100 operates. System 100 includes an implantable system 105, an external system 115, and a telemetry link 112 providing for communication between implantable system 105 and external system 115.

Implantable system 105 includes an implantable medical device 110 and a lead system 108. In various embodiments, implantable medical device 110 is an implantable CRM device including a pacemaker and one or more of a cardioverter/defibrillator, a cardiac resynchronization therapy (CRT) device, a cardiac remodeling control therapy (RCT) device, a neurostimulator, a drug delivery device or a drug delivery controller, and a biological therapy device. As illustrated in FIG. 1, implantable medical device 110 is implanted in a patient's body 102. In various embodiments, lead system 108 includes leads for sensing physiological signals and delivering pacing pulses, cardioversion/defibrillation shocks, neurostimulation, pharmaceutical agents, biological agents, and/or other types of energy or substance for treating cardiac disorders. In various embodiments, electrodes placed in the patient's heart 101 or other portions of body 102 are used to sense physiological signals and deliver pacing pulses, cardioversion/defibrillation shocks, neurostimulation, pharmaceutical agents, biological agents, and/or other types of energy or substance for treating cardiac disorders. In one embodiment, lead system 108 includes one or more pacing-sensing leads each including at least one electrode placed in or on heart 101 for sensing one or more electrograms and/or delivering pacing pulses. In one embodiment, lead system 108 allows pacing pulses to be delivered to multiple atrial and ventricular sites.

Implantable medical device 110 including a pacing and monitoring system 120 that delivers one or more cardiac pacing therapies, such as the stress augmentation pacing therapy, bradycardia pacing therapy, CRT, and RCT. In one embodiment, in addition to pacing, implantable medical device 110 controls delivery of one or more of other therapies such as neurostimulation therapy, drug therapy, and biologic therapy in coordination with a cardiac pacing therapy. Following a vagal surge event, system 120 monitors one or more signals indicative of the vagal surge and adjusts delivery of pacing therapy to maximize the therapeutic benefit of the vagal surge. The vagal surge event includes an event associated with increased activity in the vagus nerve, which is indicated by a lower intrinsic heart rate, among other physiologic parameters. In one embodiment, the vagal surge event results from delivery of pacing, neurostimulation, drug, or biological therapy from implantable medical device 110 or another implantable or non-implantable medical device. In one embodiment, system 120 intermittently delivers stress augmentation pacing sessions to heart 101 while providing post-session monitoring and therapy adjustments to maximize the therapeutic benefit of vagal surge resulting from the stress augmentation pacing. Various embodiments of pacing and monitoring system 120 are further discussed below in this document.

Implantable medical device 110 includes a hermetically sealed can to house electronic circuitry that performs sensing and therapeutic functions. In one embodiment, system 120 is housed within the hermetically sealed can. In another embodiment, system 120 includes internal components housed within the hermetically sealed can and external components located external to the hermetically sealed can but communicatively coupled to the internal components. In another embodiment, system 120 includes components external to implantable medical device 110.

External system 115 allows a user such as a physician or other caregiver or the patient to control the operation of implantable medical device 110 and obtain information acquired by implantable medical device 110. In one embodiment, external system 115 includes a programmer communicating with implantable medical device 110 bi-directionally via telemetry link 112. In another embodiment, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor and treat a patient from a distant location.

Telemetry link 112 provides for data transmission from implantable medical device 110 to external system 115. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver one or more therapies.

Figure 2:
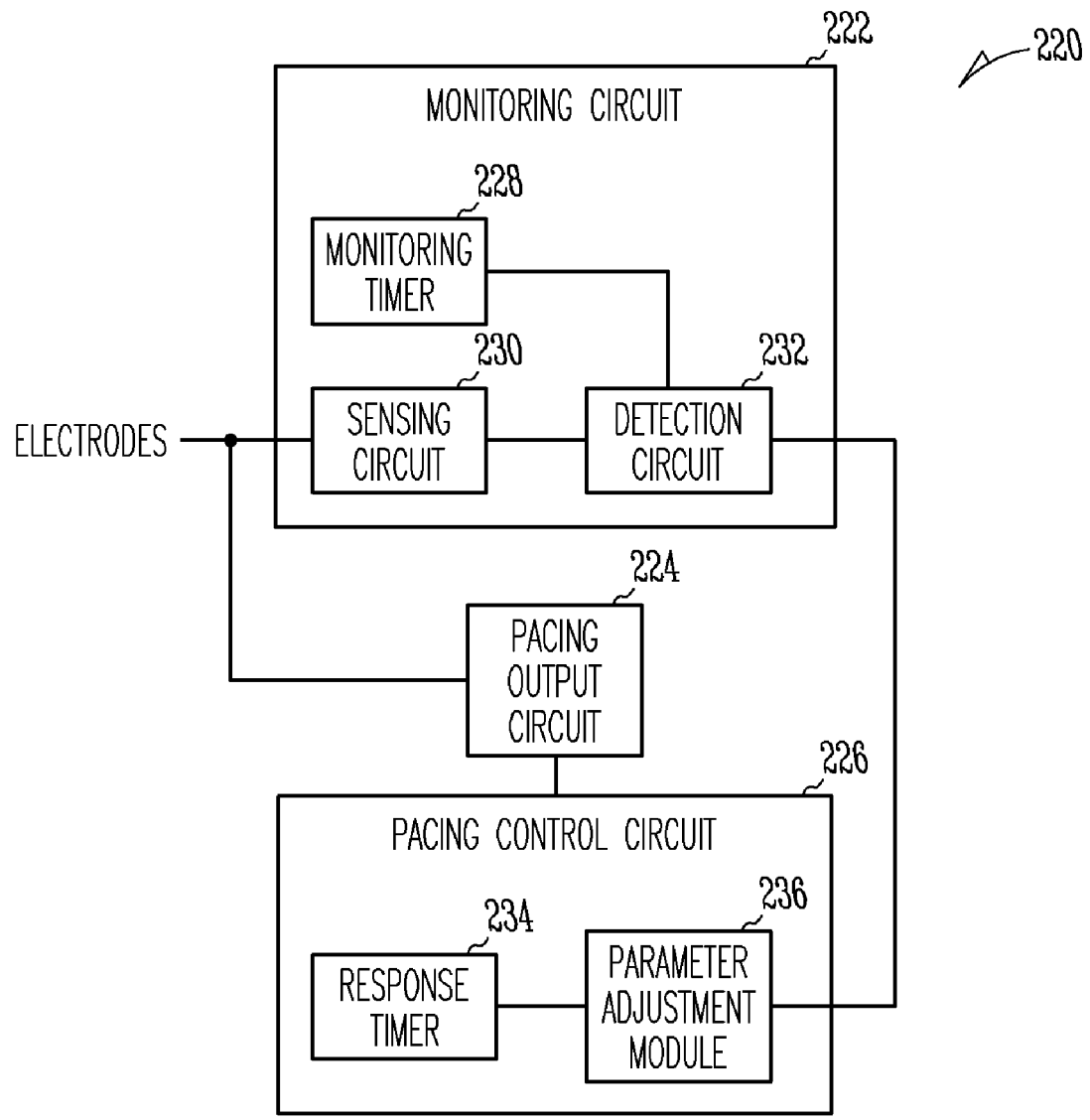
FIG. 2 is a block diagram illustrating an embodiment of a pacing and monitoring system of the CRM system.

FIG. 2 is a block diagram illustrating an embodiment of a pacing and monitoring system 220. System 220 is an embodiment of system 120 and includes a monitoring circuit 222, a pacing output circuit 224, and a pacing control circuit 226. In various embodiments, system 220 monitors a patent's conditions and delivers pacing therapy to the patent.

Monitoring circuit 222 includes a monitoring timer 228, a sensing circuit 230, and a detection circuit 232. Monitoring timer 228 times a monitoring interval that includes an anticipated duration of vagal surge resulting from a specified type event. In various embodiments, the anticipated duration of vagal surge includes a time interval during which vagal surge is expected to be substantially detectable and/or associated with substantial therapeutic benefit to the patient. In various embodiments, the specific type event is a vagal surge event such as a delivery of therapy to the patient with vagal surge being an intended or otherwise anticipated effect in the patient. Sensing circuit 230 senses one or more physiological signals each indicative of a level of vagal surge in the patient. Detection circuit 232 detects one or more parameters each indicative of the level of vagal surge using the sensed one or more physiological signals. In one embodiment, sensing circuit 230 senses at least a cardiac signal, and detection circuit 232 detects at least an intrinsic heart rate of the patient using the cardiac signal.

Pacing output circuit 224 delivers pacing pulses to the patient's heart. Pacing control circuit 226 controls the delivery of the pacing pulses using pacing parameters and includes a response timer 234 and a parameter adjustment module 236. Response timer 234 times a response interval following the specified type event. The response interval includes the anticipated duration of vagal surge resulting from the specified type event. Parameter adjustment module 236 adjusts one or more of the pacing parameters to allow the patient's heart to beat at its intrinsic heart rate (sinus rate) during the response interval.

In various embodiments, system 220, including its various elements in various embodiments, is implemented using a combination of hardware and software. In various embodiments, each element of system 220 may be implemented using an application-specific circuit constructed to perform one or more specific functions or a general-purpose circuit programmed to perform such function(s). Such a general-purpose circuit includes, but is not limited to, a microprocessor or a portion thereof, or other programmable logic circuit or a portion thereof. In one embodiment, monitoring circuit 222 and pacing control circuit 226, or portions thereof, including their elements in various embodiments, are implemented as a microprocessor-based circuit programmed to perform various functions selected from those discussed in this document.

Figure 3:
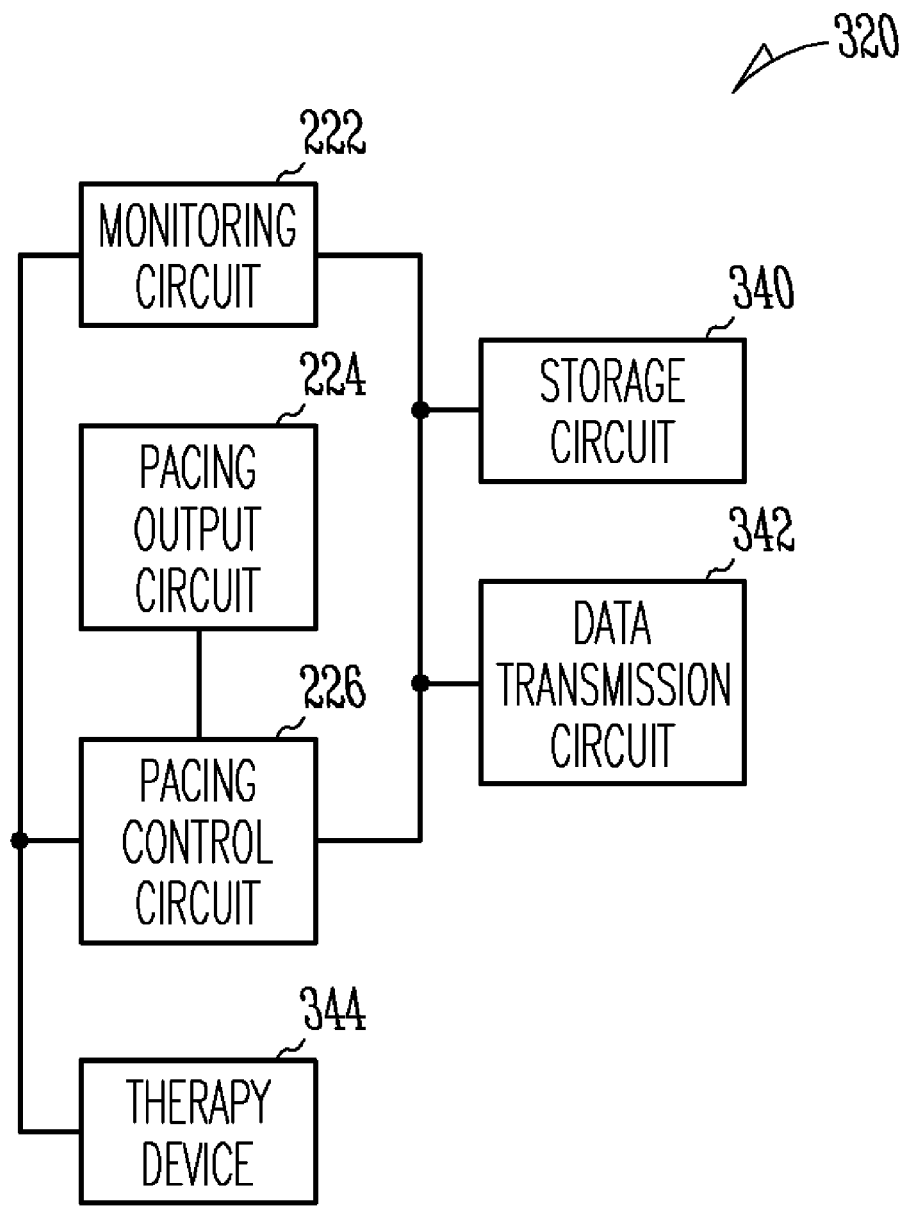
FIG. 3 is a block diagram illustrating another embodiment of the pacing and monitoring system.

FIG. 3 is a block diagram illustrating an embodiment of a pacing and monitoring system 320. System 320 is an embodiment of system 220 and includes monitoring circuit 222, pacing output circuit 224, pacing control circuit 226, a storage circuit 340, a data transmission circuit 342, and a therapy device 344.

The sensed one or more signals and/or the detected one or more parameters indicate therapeutic effects of the specified type event. In one embodiment, storage circuit 340 stores the one or more signals and/or the one or more parameters, to be retrieved later to allow for analysis of the therapeutic effects, including the vagal surge, of the specified type event by a physician or other caregiver. Data transmission circuit 342 transmits data representative of the one or more signals and/or the one or more parameters to a device remote from monitoring circuit 222. The device provides the physician or other caregiver with access to system 320.

Therapy device 344 performs delivery of a therapy being the specified type event. In one embodiment, monitoring timer 228 initiates the monitoring interval before or at the beginning of the delivery of the therapy. In various embodiments, therapy device 344 delivers a pacing therapy, a neurostimulation therapy, a drug therapy, and/or a biologic therapy, each as a specified type event with vagal surge being an intended or otherwise anticipated effect. In one embodiment, therapy device 344 delivers an intermittent cardiac stress augmentation pacing therapy as the specified type event. An example of the intermittent cardiac stress augmentation pacing is discussed in U.S. patent application Ser. No. 61/181,991, entitled "METHOD AND APPARATUS FOR SAFE AND EFFICIENT DELIVERY OF CARDIAC STRESS AUGMENTATION PACING", filed on May 28, 2009, assigned to Cardiac Pacemakers, Inc., which is incorporated herein by reference in its entirety. In a specific embodiment, pacing output circuit 224 and pacing control circuit 226 are part of therapy device 344 that delivers the intermittent cardiac stress augmentation pacing therapy. In one embodiment, therapy device 344 delivers a neurostimulation therapy as the specified type event. An example of such neurostimulation is an intermittent sympathetic stimulation therapy as discussed in U.S. patent application Ser. No. 12/397,464, entitled "SYSTEMS, DEVICES AND METHODS FOR MODULATING AUTONOMIC TONE", filed on Mar. 4, 2009, assigned to Cardiac Pacemakers, Inc., which is incorporated herein by reference in its entirety.

Figure 4:
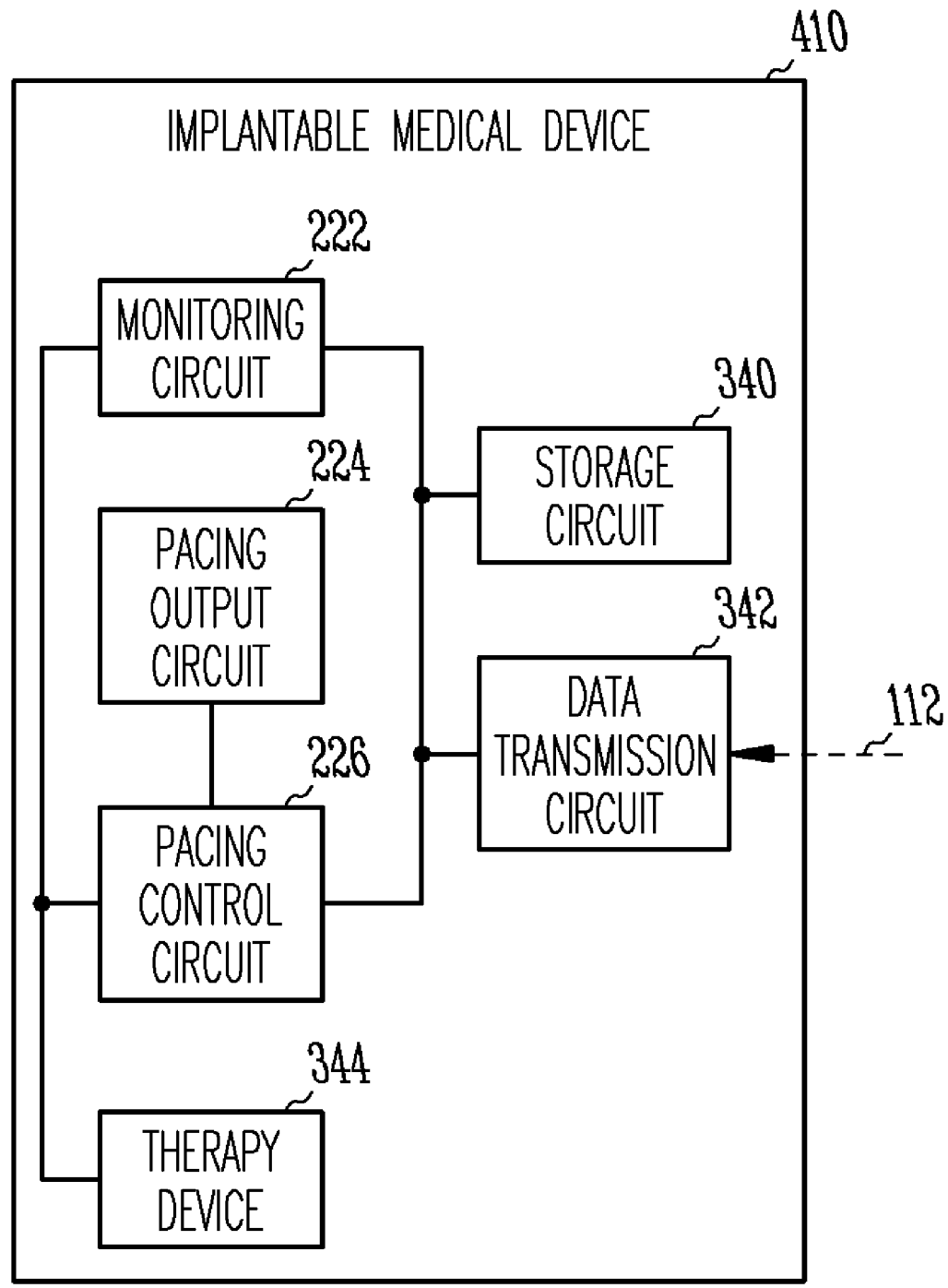
FIG. 4 is a block diagram illustrating an embodiment of distribution of the pacing and monitoring system.
Figure 5:
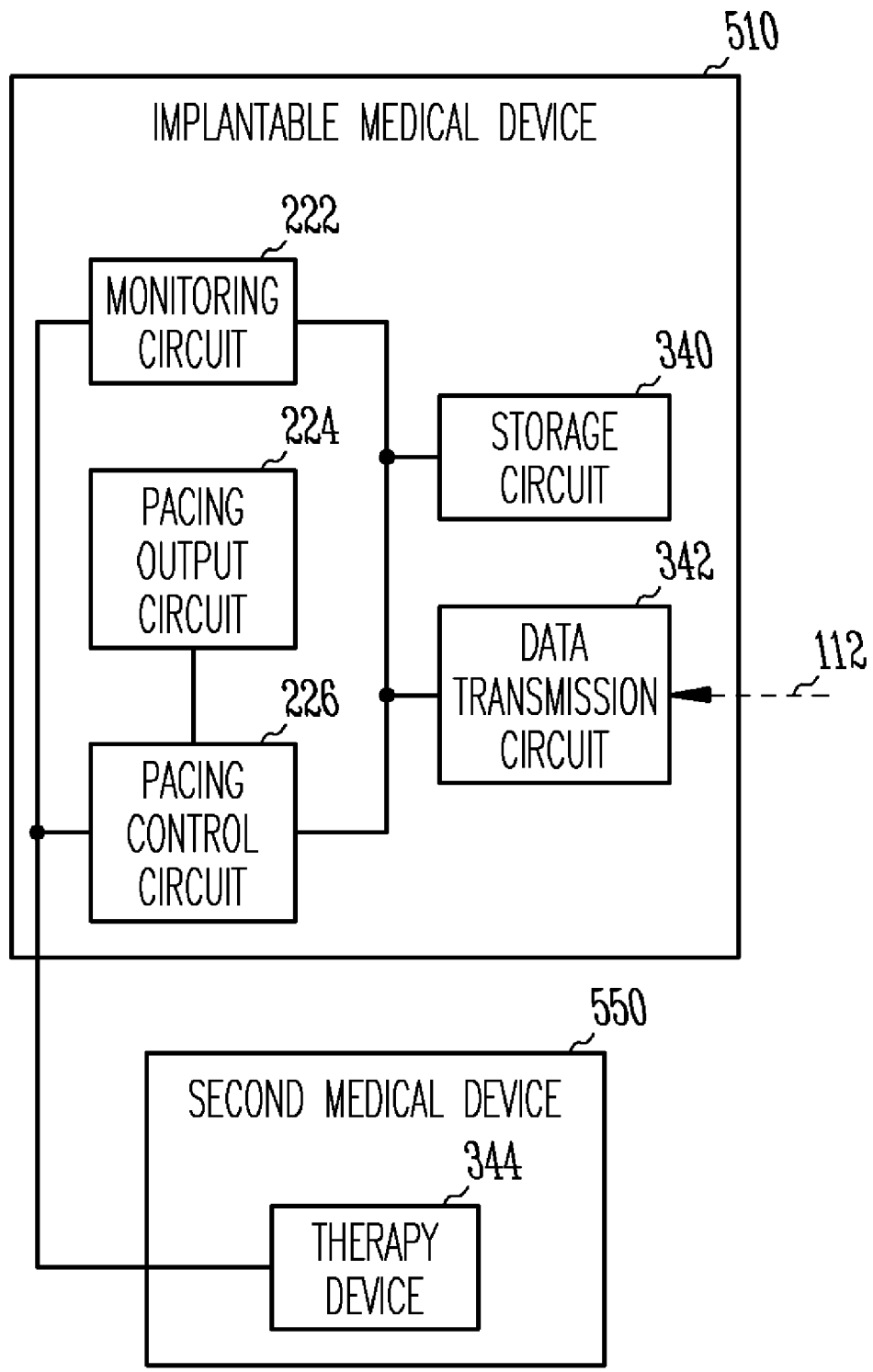
FIG. 5 is a block diagram illustrating another embodiment of distribution of the pacing and monitoring system.
Figure 6:
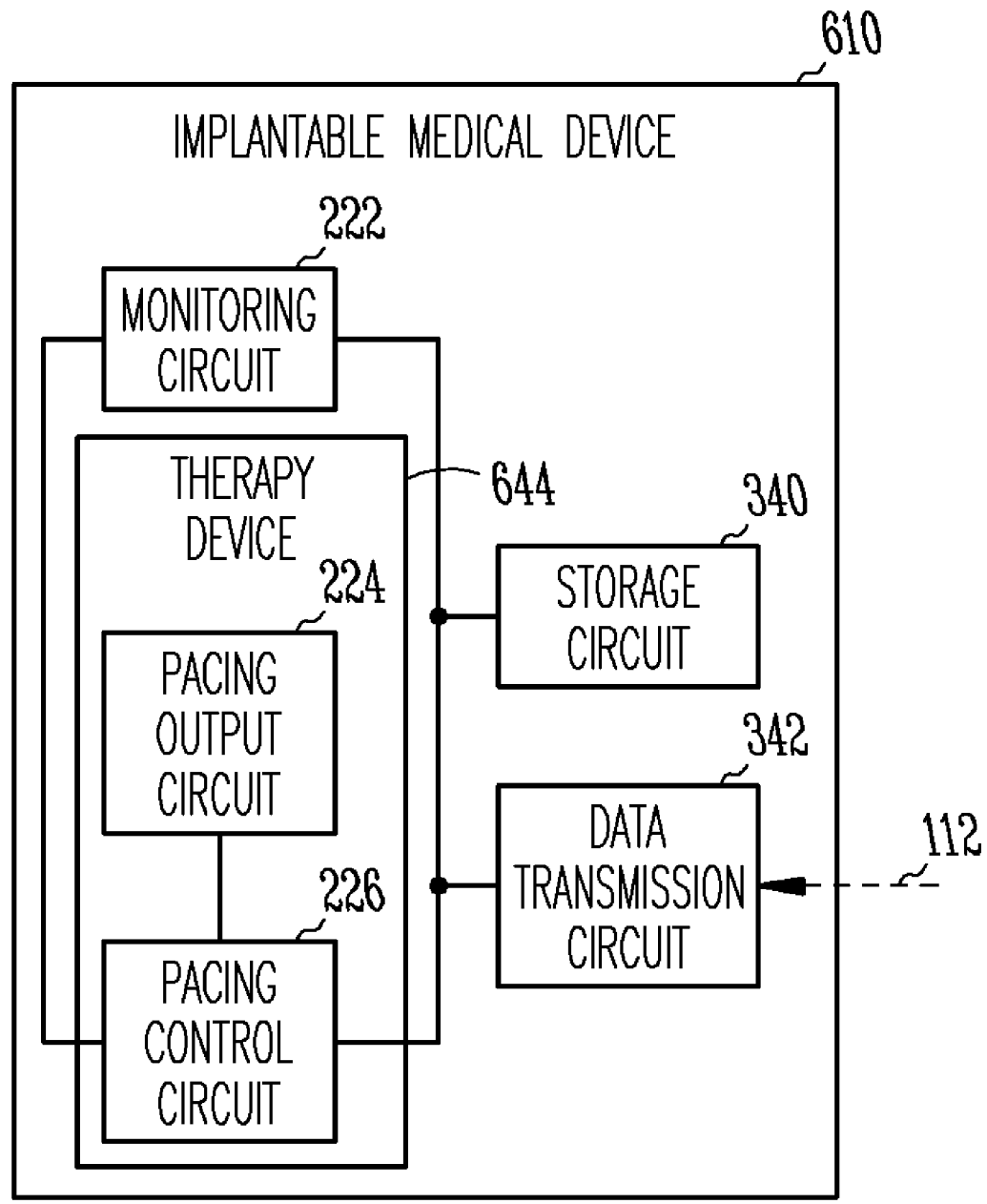
FIG. 6 is a block diagram illustrating another embodiment of distribution of the pacing and monitoring system.

FIGS. 4-6 are block diagrams each illustrating an embodiment of distribution of pacing and monitoring system 320 by way of example and not by way of limitation. In an embodiment, as illustrated in FIG. 4, an implantable medical device 410, which is an embodiment of implantable medical device 110, includes monitoring circuit 222, pacing output circuit 224, pacing control circuit 226, storage circuit 340, data transmission circuit 342, and therapy device 344. Data transmission circuit 342 transmits the data representative of the one or more signals and/or the one or more parameters to external system 115 via telemetry link 112.

In another embodiment, as illustrated in FIG. 5, an implantable medical device 510, which is another embodiment of implantable medical device 110, includes monitoring circuit 222, pacing output circuit 224, pacing control circuit 226, storage circuit 340, and data transmission circuit 342. Data transmission circuit 342 transmits the data representative of the one or more signals and/or the one or more parameters to external system 115 via telemetry link 112. A second medical device 550 includes therapy device 344. In various embodiments, second medical device 550 includes another implantable medical device or a non-implantable medical device. In various embodiments, the non-implantable medical device may include a device that is continuously worn or carried by the patient, or coupled to the patient only during the delivery of the therapy.

In another embodiment, as illustrated in FIG. 6, an implantable medical device 610, which is an embodiment of implantable medical device 110, includes monitoring circuit 222, storage circuit 340, data transmission circuit 342, and a therapy device 644. Data transmission circuit 342 transmits the data representative of the one or more signals and/or the one or more parameters to external system 115 via telemetry link 112. Therapy device 644 is an embodiment of therapy device 344 and includes pacing output circuit 224 and pacing control circuit 226. In one embodiment, the patient receives a chronic pacing therapy and an intermittent pacing therapy delivered from pacing output circuit 224 and controlled by pacing control circuit 226. Each delivery of the intermittent pacing therapy is a specified type event that results in vagal surge. Delivery of the chronic pacing therapy is paused for each delivery of the intermittent pacing therapy. When the delivery of the chronic pacing is resumed upon completion of the delivery of the intermittent pacing therapy, its pacing parameters are temporally adjusted to maximize the therapeutic benefit of the intermittent pacing therapy for the duration for which vagal surge is anticipated.

Figure 7:
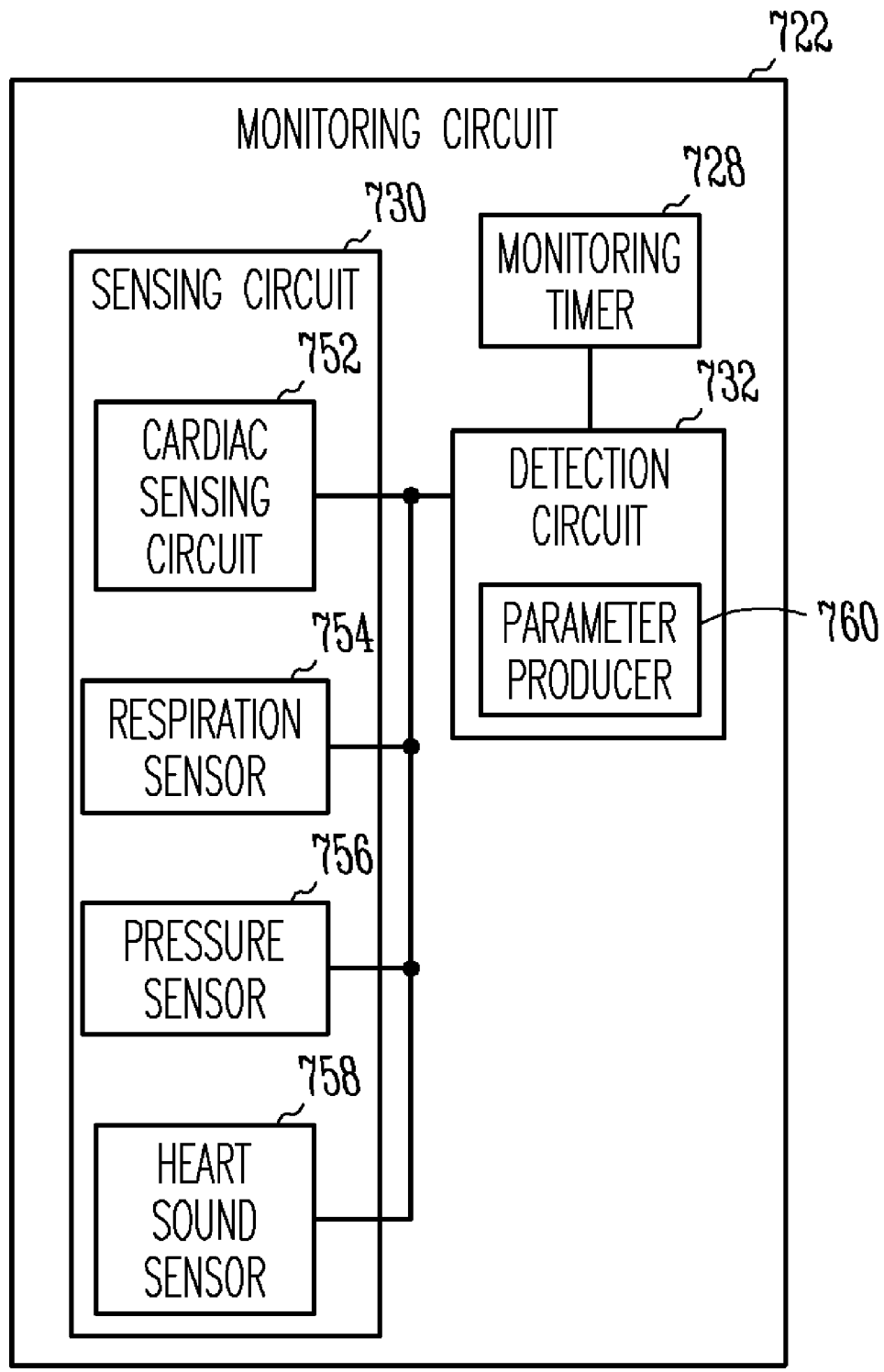
FIG. 7 is a block diagram illustrating an embodiment of a monitoring circuit of the pacing and monitoring system.

FIG. 7 is a block diagram illustrating an embodiment of a monitoring circuit 722. Monitoring circuit 722 is an embodiment of monitoring circuit 222 and includes a monitoring timer 728, a sensing circuit 730, and a detection circuit 732.

Monitoring timer 728 is an embodiment of monitoring timer 228 and times the monitoring interval that includes the anticipated duration of vagal surge resulting from the specified type event. In one embodiment, monitoring timer 728 initiates the monitoring interval at the beginning of the specified type event. In another embodiment, monitoring timer 728 initiates the monitoring interval prior to the beginning of the specified type event. In another embodiment, monitoring timer 728 initiates the monitoring interval after the beginning of the specified type event and before the anticipated vagal surge occurs. In various embodiments, the monitoring interval is experimentally determined. In one embodiment, the monitoring interval is programmable between approximately 2 to 3 hours.

Sensing circuit 730 is an embodiment of sensing circuit 230 and senses one or more physiological signals each quantitatively indicative of the level of vagal surge. In the illustrated embodiment, sensing circuit 730 includes a cardiac sensing circuit 752 to sense one or more cardiac signals indicative of cardiac depolarizations, a respiration sensor 754 such as an impedance sensor to sense a signal indicative of respiration, a pressure sensor 756 such as a pulmonary artery pressure (PAP) sensor that senses a PAP signal, a heart sound sensor 758 such as an accelerometer that senses a signal indicative of heart sounds. In various embodiments, sensing circuit 730 includes any one or more of cardiac sensing circuit 752, respiration sensor 754, pressure sensor 756, heart sound sensor 758, and other sensors suitable for sensing physiological signals indicative of vagal surge and/or cardiac contractility.

Detection circuit 732 is an embodiment of detection circuit 232 and detects one or more parameters each indicative of the level of vagal surge using the sensed one or more physiological signals. Detection circuit 732 includes a parameter producer 760 that produces one or more physiological parameters each quantitatively indicative of the level of vagal surge. In one embodiment, parameter producer 760 produces an intrinsic heart rate, an atrioventricular (AV) interval, and/or a short-term heart rate variability (HRV) indicative of heart rate turbulence (HRT) using the one or more cardiac signals, a minute ventilation using the signal indicative of respiration, a PAP or rate of change in the PAP (dPAP/dt) using the PAP signal, and a heart sound parameter using the heart sound signal. In various embodiments, parameter producer 760 produces any one or more of the intrinsic heart rate, AV interval, short-term HRV, minute ventilation, PAP, dPAP/dt, heart sound parameter, and other parameters suitable for indicating vagal surge and/or cardiac contractility.

In various embodiments, parameter producer 760 produces a pre-event value of each of the one or more parameters before the specified type event and a post-event value of each of the one or more parameters after the specified event during the monitoring interval. In one embodiment, the pre-event value is an average pre-event value over a specified pre-event averaging period. The post-event value is an average post-event value over a specified post-event averaging period after the end of the specified type event during the monitoring interval. In one embodiment, parameter producer 760 produces a plurality of post-event values for the each of the one or more parameters over the monitoring interval after the end of the specified type event. In a further embodiment, parameter producer 760 produces a change value of each of the one or more parameters. The change value is a difference between the post-event value and the pre-event value of the each of the one or more parameters. In one embodiment, parameter producer 760 produces a plurality of change values for the each of the one or more parameters over the monitoring interval after the end of the specified type event.

Figure 8:
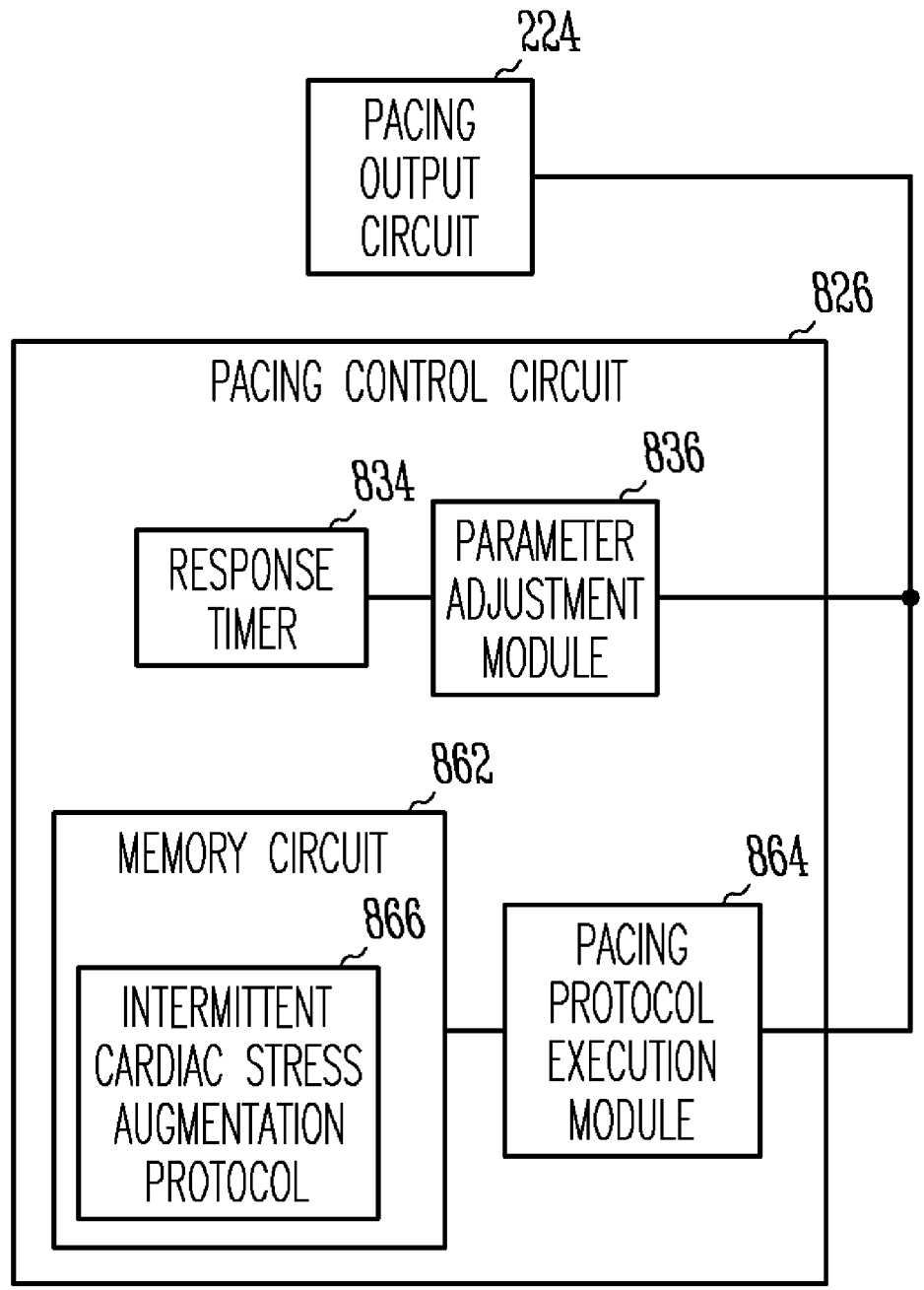
FIG. 8 is a block diagram illustrating an embodiment of a pacing output circuit and a pacing control circuit of the pacing and monitoring system.

FIG. 8 is a block diagram illustrating an embodiment of pacing output circuit 224 and pacing control circuit 826. Pacing control circuit 826 is an embodiment of pacing control circuit 226 for use in implantable medical device 610 as illustrated in FIG. 6, in which the specified type event is a delivery of pacing therapy. Pacing controller 826 includes a response timer 834, a parameter adjustment module 836, a memory circuit 862, and a pacing protocol execution module 864.

Response timer 834 is an embodiment of response timer 234 and times a response interval following the specified type event. The response interval includes the anticipated duration of vagal surge resulting from the specified type event. In one embodiment, response timer 834 initiates the response interval in response to the end of the specified type event. In one embodiment, response timer 834 initiates the response interval upon expiration of a delay interval starting at the end of the specified type event. In one embodiment, the response interval is programmable between approximately 2 and 3 hours, and the delay is programmable between approximately 0 and 10 minutes. In one embodiment, response timer 834 terminates the response interval before or at the termination of the monitoring interval.

Parameter adjustment module 836 is an embodiment of parameter adjustment module 236 and adjusts one or more of the pacing parameters to allow the heart to beat at the intrinsic heart rate during the response interval. This allows for measurement of the intrinsic heart rate and maximization of therapeutic benefits of the vagal surge. In one embodiment, parameter adjustment module 836 lowers a lower rate limit (LRL) to a rate lower than the detected intrinsic heart rate by a specified margin during the response interval. In one embodiment, the margin is specified to be approximately 15 beats per minute (bpm). In one embodiment, pacing control circuit 826 lowers the LRL during the response interval if the LRL is set to at least a minimum value before it is lowered, such as approximately 70 bpm, to ensure patient safety. If the LRL is already set to a low value to promote an intrinsic sinus rhythm during the chronic pacing therapy, there may not be a need to adjust the LRL during the response interval.

An intermittent cardiac stress augmentation pacing protocol 866 is stored in memory circuit 862. Pacing protocol execution module 864 controls the delivery of the pacing pulses by executing pacing protocols including intermittent cardiac stress augmentation pacing protocol 866.

In one embodiment, intermittent cardiac stress augmentation pacing protocol 866 specifies stress augmentation pacing sessions each being a specified type event and including alternating non-pacing and pacing periods. The non-pacing periods each have a non-pacing duration during which no pacing pulse is timed to be delivered. The pacing periods each have a specified pacing duration during which a plurality of the pacing pulses is timed to be delivered using pacing parameters selected to augment cardiac stress to the level effective in slowing or stopping progression of the cardiac disorder.

In another embodiment, intermittent cardiac stress augmentation pacing protocol 866 specifies stress augmentation pacing sessions each being a specified type event and including alternating first and second pacing periods. The first pacing periods each have a first pacing duration during which a plurality of the pacing pulses is timed to be delivered according to a first pacing mode. The second pacing periods each have a second pacing duration during which a plurality of the pacing pulses is timed to be delivered according to a second pacing mode including pacing parameters selected to augment cardiac stress to the level effective in slowing or stopping progression of the cardiac disorder.

Figure 9:
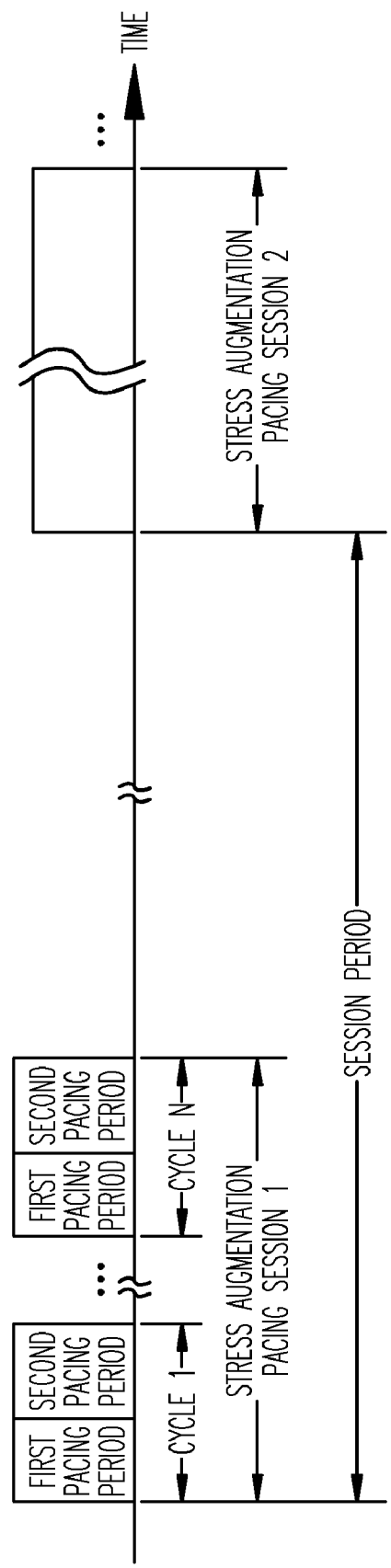
FIG. 9 is a timing diagram illustrating an embodiment of timing of an intermittent cardiac stress augmentation pacing protocol specifying stress augmentation pacing sessions.

FIG. 9 is a timing diagram illustrating an embodiment of timing of an intermittent cardiac stress augmentation pacing protocol specifying stress augmentation pacing sessions, such as intermittent cardiac stress augmentation pacing protocol 866. The stress augmentation pacing, also known as intermittent pacing and cardioprotective pacing, protects the heart from cardiac disorders such as ischemia, infarction, and heart failure by creating or augmenting regional stress in the heart for brief periods of time to activate and/or enhance the patient's intrinsic cardiac protective mechanisms. In the illustrated embodiment, the intermittent cardiac stress augmentation pacing protocol specifies stress augmentation pacing sessions delivered on a periodic basis at a session frequency (or period as marked in FIG. 9). Each stress augmentation pacing session includes N cycles of alternating first and second pacing periods. Each cycle includes a first pacing period followed by a second pacing period. The first pacing period has a first pacing duration during which the delivery of the pacing pulses is controlled according to a first pacing mode. The second pacing period has a second pacing duration during which the delivery of the pacing pulses is controlled according to the second pacing mode.

In one embodiment, the first pacing period is a non-pacing period having a first pacing duration during which no pacing pulse is timed to be delivered according to a non-pacing mode, and the second pacing period is a stress augmentation pacing period having a second pacing duration during which pacing pulses are timed to be delivered according to a stress augmentation pacing mode. When a pacing pulse is timed to be delivered, it will be delivered unless being inhibited by a detected intrinsic cardiac depolarization occurring before the scheduled delivery of the pacing pulse during a cardiac cycle. Under the non-pacing mode according to which no pacing pulse is timed to be delivered, the non-delivery is due to programming rather than inhibition by a detected intrinsic cardiac depolarization. Under the stress augmentation pacing mode, pacing pulses are delivered to augment mechanical stress on the myocardium to a level effecting cardioprotection against myocardial injury or deterioration. In various embodiments, the stress augmentation pacing mode is a standard or non-standard pacing mode with pacing parameter values selected for the desired level of myocardial stress augmentation according to the patients' needs, conditions, and responses. In one embodiment, the stress augmentation pacing mode is an atrial tracking pacing mode with an AV delay that is substantially shorter than the patient's intrinsic AV conduction interval. In another embodiment, the stress augmentation pacing mode is a bradycardia pacing mode with a pacing rate substantially higher than the patient's intrinsic heart rate. In another embodiment, the stress augmentation pacing mode is an asynchronous pacing mode with a pacing rate substantially higher than the patient's intrinsic heart rate.

In another embodiment, the first pacing period is a back-up pacing period having a first pacing duration during which pacing pulses are timed to be delivered according to a back-up pacing mode, and the second pacing period is a stress augmentation pacing period having a second pacing duration during which the delivery of the pacing pulse is controlled according to the stress augmentation pacing mode. In one embodiment, the backup pacing mode is a chronic pacing mode that is substantially different from the stress augmentation pacing mode and applied before and/or after the stress augmentation pacing session. In one embodiment, the back-up pacing mode is an anti-bradycardia pacing mode according to which pacing pulses are timed to be delivered as an anti-bradycardia therapy. In another embodiment, the back-up pacing mode is a cardiac resynchronization mode according to which pacing pulses are timed to be delivered as a CRT. In another embodiment, the back-up pacing mode is a cardiac remodeling control mode according to which pacing pulses are timed to be delivered as a RCT.

In various embodiments, the session frequency (or period), the number of the cycles (N), the first pacing period, and the second pacing period are each programmable. In one embodiment, the session frequency is programmable between approximately 1 and 12 sessions each day. The number of cycles (N) for each stress augmentation pacing session is programmable between approximately 3 and 12 cycles. The first and second pacing periods are each programmable between approximately 5 and 16 minutes. In one embodiment, the first pacing duration is substantially equal to the second pacing duration. In various embodiments, the values of these parameters are determined based on the patient's physiological and pathological conditions, tolerance to the stress augmentation pacing therapy, and responsiveness to the stress augmentation pacing therapy known to associate with certain values or value ranges of the parameters. For example, the patient may need a relatively large number of stress augmentation pacing sessions each with a relatively low intensity (i.e., relatively low level of elevation or duration of cardiac stress augmentation), or a relatively small number of stress augmentation pacing sessions each with a relatively high intensity.

Figure 10:
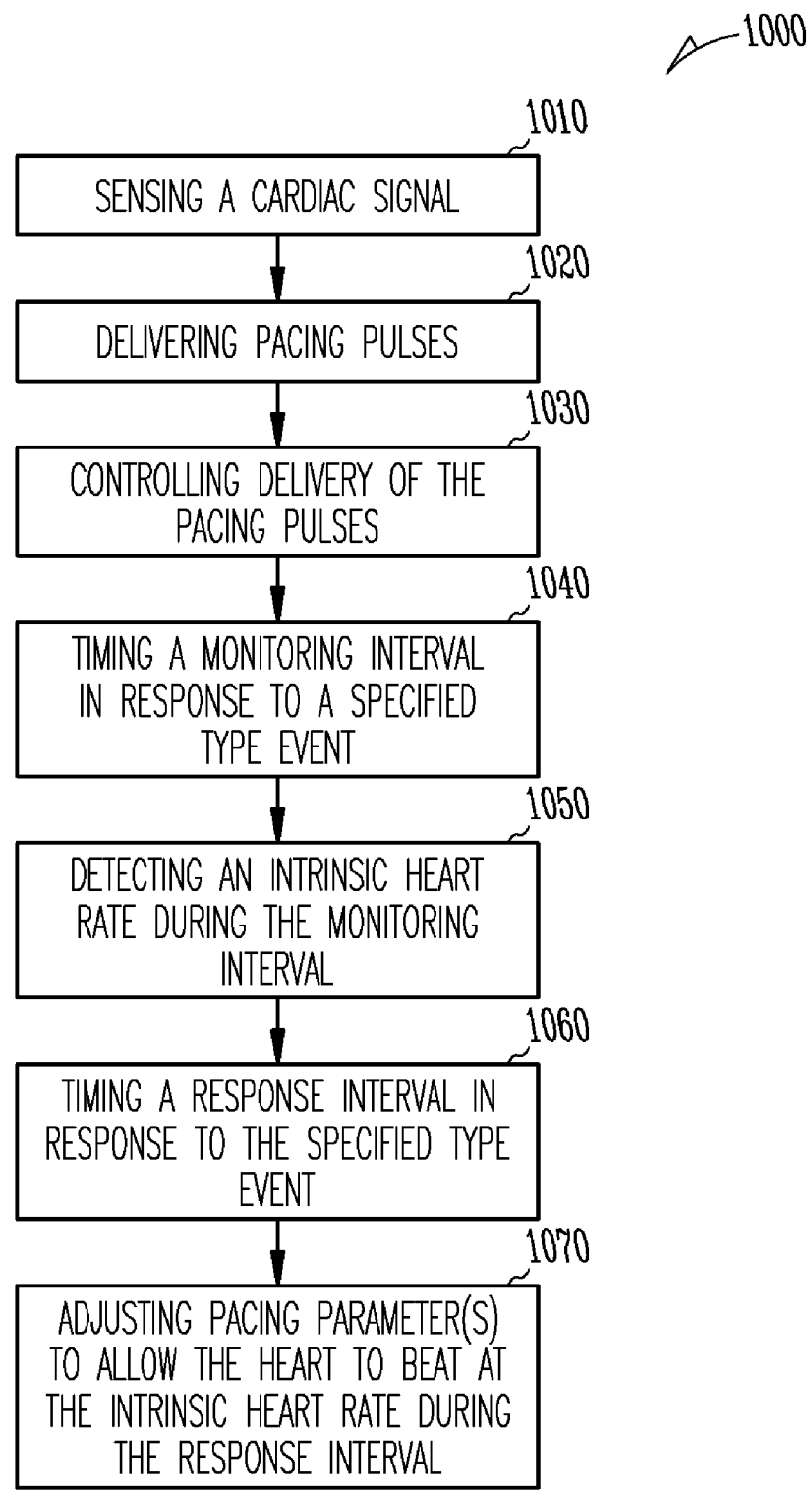
FIG. 10 is a flow chart illustrating an embodiment of a method for operating a CRM system.

FIG. 10 is a flow chart illustrating an embodiment of a method 1000 for operating a CRM system. In one embodiment, the CRM system is system 100, including the various embodiments of its components as discussed in this document.

At 1010, a cardiac signal is sensed from a patient's heart. At 1020, pacing pulses are delivered to the patient's heart. In one embodiment, the pacing pulses are delivered to the patient's heart as a chronic pacing therapy. At 1030, the delivery of the pacing pulses is controlled using pacing parameters selected according to a pacing mode specified for the chronic pacing therapy.

At 1040, a monitoring interval is timed in response to a specified type event. The monitoring interval is associated with and includes an anticipated duration of vagal surge resulting from the specified type event. In one embodiment, the monitoring interval is initiated at the beginning of the specified event. In one embodiment, the specified type event is the delivery of a temporary pacing therapy. In other embodiments, the specified type event is a neurostimulation, drug, or biologic therapy that enhances cardiac contractility. In various embodiments, the monitoring interval is experimentally determined. In one embodiment, the monitoring interval is programmed to a time interval between approximately 2 to 3 hours.

At 1050, an intrinsic heart rate is detected from the cardiac signal during the monitoring interval. The intrinsic heart rate indicates the level of vagal surge. In various embodiments, additional one or more physiological signals each indicative of the level of vagal surge are sensed during the monitoring interval. Examples of such one or more physiological signals include a respiration signal, a pulmonary artery pressure (PAP) signal, and a heart sound signal. Additional one or more parameters each indicative of the level of vagal surge are produced using the cardiac signal or the additional one or more physiological signals. Examples of such one or more parameters include an AV interval, a short-term HRV indicative of HRT, a minute ventilation, a PAP, a rate of change in the PAP (dPAP/dt), and a heart sound parameter. In one embodiment, a pre-event value of each of the one or more parameters is produced before the specified type event, and a post-event value of each of the one or more parameters is produced after the specified type event during the monitoring interval. In one embodiment, the pre-event value is an average pre-event value over a specified pre-event averaging period, and the post-event value is an average post-event value over a specified post-event averaging period after the end of the specified type even during the monitoring interval t. In one embodiment, a plurality of post-event values is produced for the each of the one or more parameters over the monitoring interval after the end of the specified type event. In a further embodiment, a change value of each of the one or more parameters is produced. The change value is a difference between the post-event value and the pre-event value of the each of the one or more parameters. In one embodiment, a plurality of change values is produced for the each of the one or more parameters over the monitoring interval after the end of the specified type event. Such one or more signals and/or the one or more parameters allow for analysis of therapeutic effects of the specified type event.

At 1060, a response interval is timed in response to the specified type event. The response interval includes the anticipated duration of vagal surge resulting from the specified type event. In one embodiment, the response interval is initiated in response to the end of the specified type event. In one embodiment, the response interval is initiated upon expiration of a delay interval starting at the end of the specified type event. In one embodiment, the response interval is programmed to a time interval between approximately 2 and 3 hours, and the delay interval is programmed to a time interval between approximately 0 and 10 minutes. In one embodiment, the response interval and the monitoring interval are programmed to terminate approximately simultaneously. In one example, the monitoring interval and the response time are programmed to terminate simultaneously at approximately 2 to 3 hours following the end of the specified type event.

At 1070, one or more pacing parameters are adjusted to allow the heart to beat at the intrinsic heart rate during the response interval. This allows measurement of the intrinsic heart rate and maximization of therapeutic benefit from the vagal surge. In one embodiment, an LRL is lowered during the response interval by a specified margin, such as approximately 15 bpm. In one embodiment, to ensure patient safety, the LRL is lowered during the response interval if the LRL is set to at least a minimum value (before lowering) for the chronic pacing therapy, such as approximately 70 bpm. If the LRL for the chronic therapy is already set to a low value to promote an intrinsic sinus rhythm, further lowing of the LRL may not be necessary.

Figure 11:
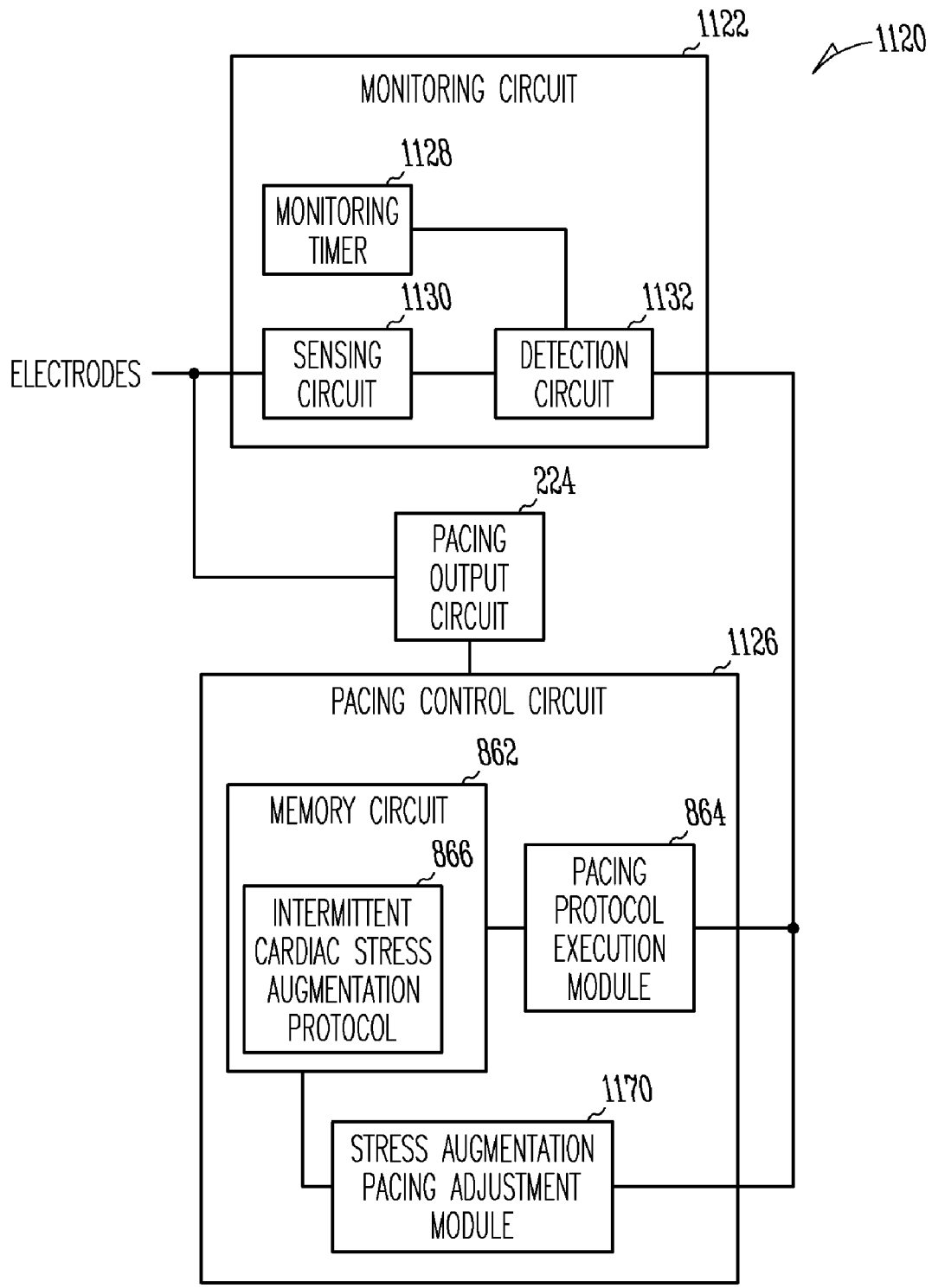
FIG. 11 is a block diagram illustrating an embodiment of a pacing and monitoring system providing for adjustment of the intermittent cardiac stress augmentation pacing protocol.

FIG. 11 is a block diagram illustrating an embodiment of a pacing and monitoring system 1120. System 1120 is an embodiment of system 120 and includes a monitoring circuit 1122, pacing output circuit 224, and a pacing control circuit 1126. In one embodiment, system 1120 performs the functions of system 220, with the specific type event being a stress augmentation pacing session specified in an intermittent cardiac stress augmentation pacing protocol such as intermittent cardiac stress augmentation pacing protocol 866. In addition, system 1120 provides for adjustment of the intermittent cardiac stress augmentation pacing protocol using the acute response of the patient to the stress augmentation pacing session.

Monitoring circuit 1122 includes a monitoring timer 1128, a sensing circuit 1130, and a detection circuit 1132. Monitoring timer 1122 initiates and times a monitoring interval including an anticipated duration of an acute response to a stress augmentation pacing session of a plurality of stress augmentation pacing sessions. Sensing circuit 1130 senses one or more physiological signals each indicative of a level of the acute response. Detection circuit 1132 detects the acute response using the one or more physiological signals during the monitoring interval and produces an acute response signal after expiration of the monitoring interval. The acute response signal indicates a status of the acute response to the stress augmentation pacing session.

Pacing output circuit 224 delivers pacing pulses. Pacing control circuit 1126 controls the delivery of the pacing pulses from pacing output circuit 224 and includes memory circuit 862, pacing protocol execution module 864, and a stress augmentation pacing adjustment module 1170. Intermittent cardiac stress augmentation pacing protocol 866 is stored in memory circuit 862 and specifies the plurality of stress augmentation pacing sessions. In various embodiments, intermittent cardiac stress augmentation pacing protocol 866 specifies a stress augmentation pacing mode including pacing parameters selected to augment cardiac stress to the level effective in slowing or stopping progression of a cardiac disorder. Pacing protocol execution module 864 controls the delivery of the pacing pulses by executing intermittent cardiac stress augmentation pacing protocol 866. Stress augmentation pacing adjustment module 1170 adjusts intermittent cardiac stress augmentation pacing protocol 866 using the acute response signal. In one embodiment, stress augmentation pacing adjustment module 1170 approximately optimizes parameters of intermittent cardiac stress augmentation pacing protocol 866 using the acute response signal.

In various embodiments, system 1120, including its various elements in various embodiments, is implemented using a combination of hardware and software. In various embodiments, each element of system 1120 may be implemented using an application-specific circuit constructed to perform one or more specific functions or a general-purpose circuit programmed to perform such function(s). Such a general-purpose circuit includes, but is not limited to, a microprocessor or a portion thereof, or other programmable logic circuit or a portion thereof. In one embodiment, monitoring circuit 1122 and pacing control circuit 1126, or portions thereof, including their elements in various embodiments, are implemented as a microprocessor-based circuit programmed to perform various functions selected from those discussed in this document.

Figure 12:
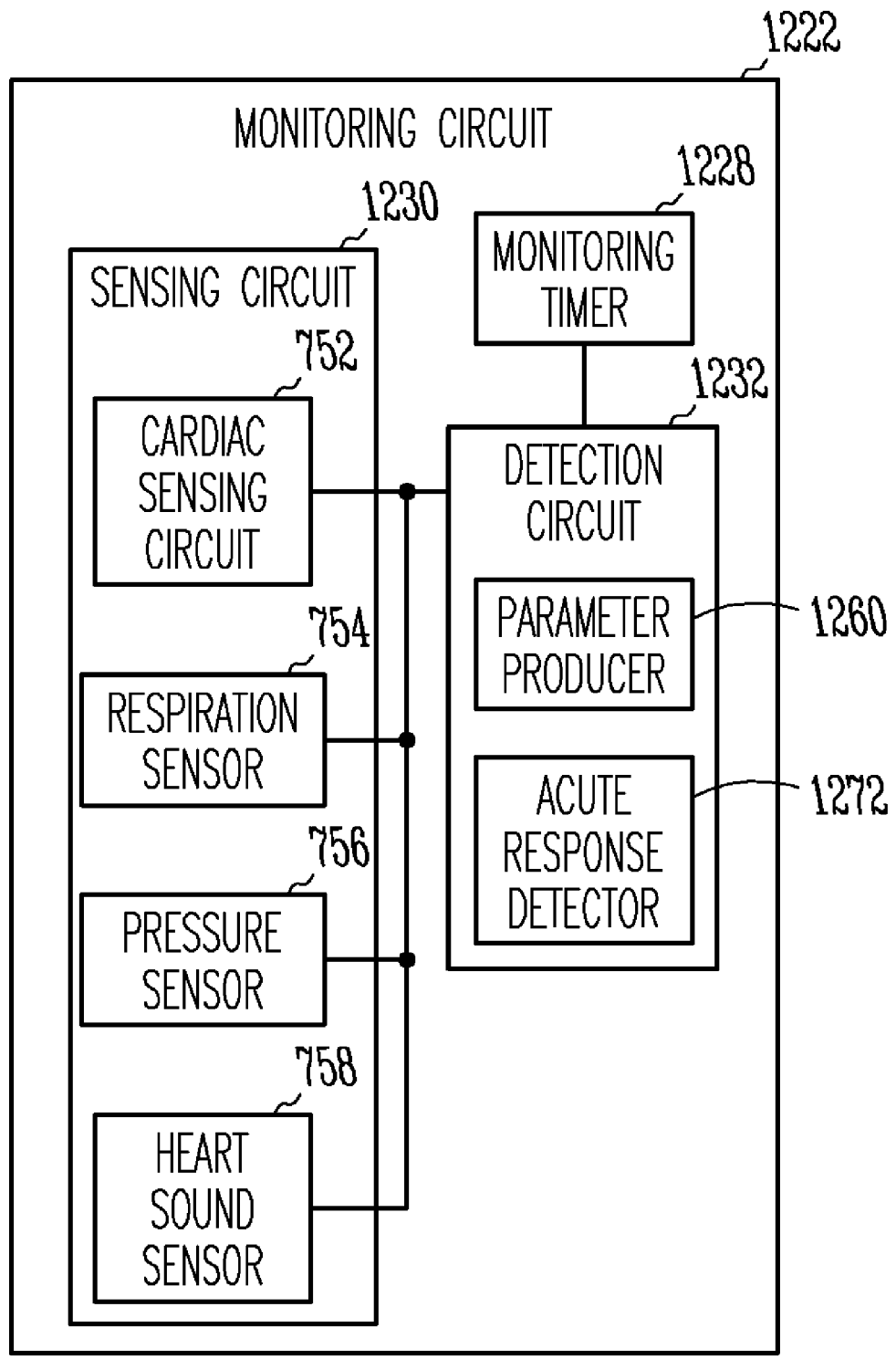
FIG. 12 is a block diagram illustrating an embodiment of a monitoring circuit of the pacing and monitoring system of FIG. 11.

FIG. 12 is a block diagram illustrating an embodiment of a monitoring circuit 1222. Monitoring circuit 1222 is an embodiment of monitoring circuit 1122 and includes a monitoring timer 1228, a sensing circuit 1230, and a detection circuit 1232.

Monitoring timer 1228 initiates and times the monitoring interval including the anticipated duration of the acute response to the stress augmentation pacing session. In one embodiment, the acute response includes vagal surge resulting from the stress augmentation pacing session.

Sensing circuit 1230 senses the one or more physiological signals each indicative of the level of the acute response. In one embodiment, the one or more physiological signals include one or more physiological signals each indicative of a level of the vagal surge. In one embodiment, the one or more physiological signals indicative of the level of the vagal surge include at least a cardiac signal. In the illustrated embodiment, sensing circuit 1230 includes cardiac sensing circuit 752, respiration sensor 754, pressure sensor 756, and heart sound sensor 758. In various embodiments, sensing circuit 1230 includes any one or more of cardiac sensing circuit 752, respiration sensor 754, pressure sensor 756, heart sound sensor 758, and other sensors suitable for sensing physiological signals indicative of vagal surge and/or cardiac contractility.

Detection circuit 1232 detects the acute response using the one or more physiological signals during the monitoring interval and produces an acute response signal after expiration of the monitoring interval. The acute response signal indicates the status of the acute response to the stress augmentation session. In the illustrated embodiment, detection circuit 1232 includes a parameter producer 1260 and an acute response detector 1272. Parameter producer 1260 produces one or more parameters each indicative of the level of the acute response using the sensed one or more physiological signals. In one embodiment, the one or more parameters include one or more parameters each indicative of the level of the vagal surge. In one embodiment, the one or more parameters each indicative of the level of the vagal surge include at least an intrinsic heart rate. In one embodiment, parameter producer 1260 performs the functions of parameter producer 760 as discussed above. Acute response detector 1272 detects the acute response by comparing the one or more parameters to one or more thresholds and produces the acute response signal using an outcome of the comparison. In one embodiment, acute response detector 1272 declares one of presence and absence of the acute response. In one embodiment, acute response detector 1272 declares the presence or the absence of the acute response on a continuous basis during the monitoring interval. In another embodiment, acute response detector 1272 declares the presence or the absence of the acute response on a periodic basis during the monitoring interval. In one embodiment, acute response detector 1272 detects a duration of the acute response being a time interval during which the presence of the acute response is declared. In various embodiments, the acute response signal includes the one or more parameters each indicative of the level of the acute response, indication of the presence or absence of the acute response, and/or the duration of the acute response.

Figure 13:
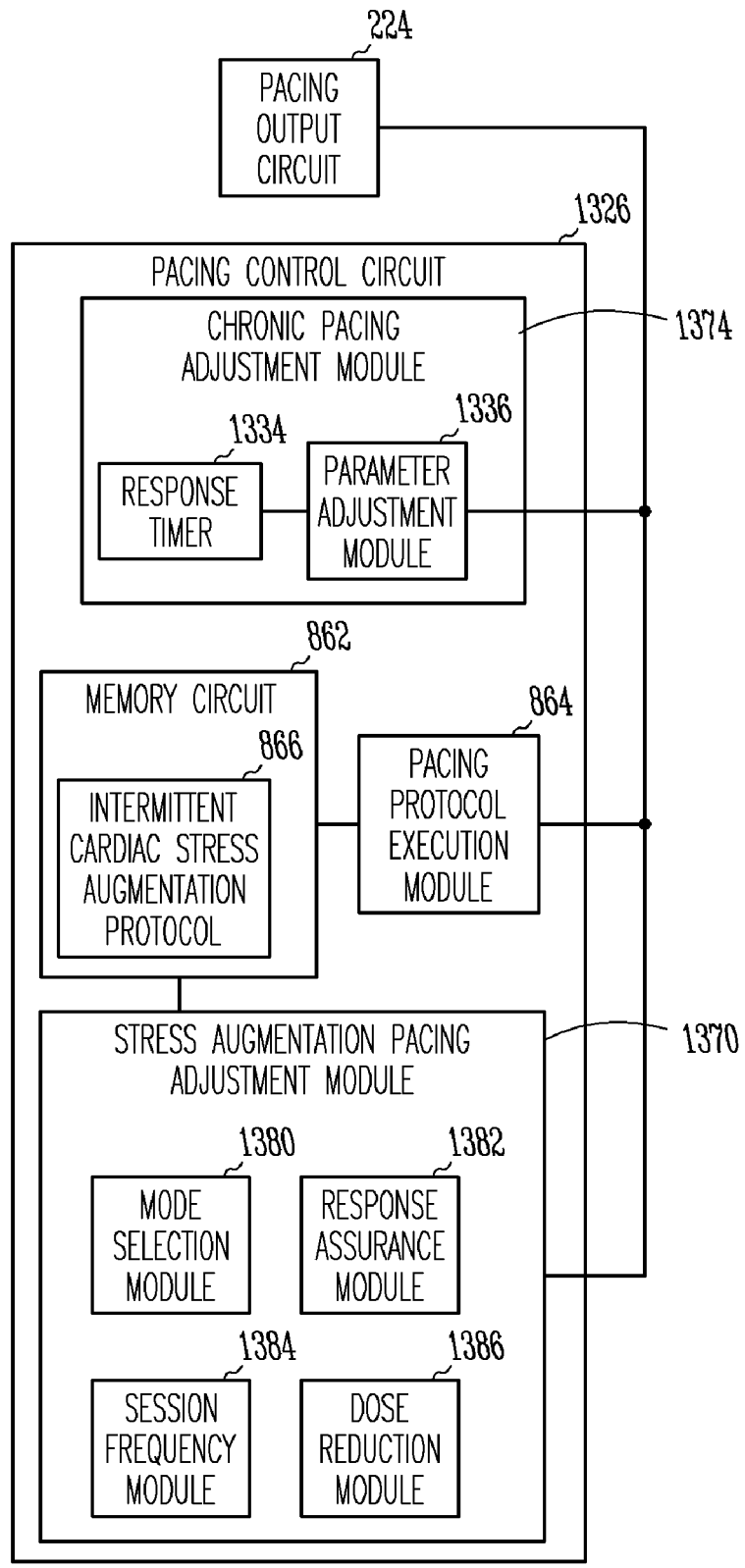
FIG. 13 is a block diagram illustrating an embodiment of a pacing output circuit and a pacing control circuit of the pacing and monitoring system of FIG. 12.

FIG. 13 is a block diagram illustrating an embodiment of pacing output circuit 224 and a pacing control circuit 1326. Pacing control circuit 1326 is an embodiment of pacing control circuit 1126 and includes memory circuit 862 storing intermittent cardiac stress augmentation pacing protocol 866, pacing protocol execution module 864, a chronic pacing adjustment module 1374, and a stress augmentation pacing adjustment module 1370.

In one embodiment, the patient receives a chronic pacing therapy that is paused for each stress augmentation pacing session of the plurality of stress augmentation pacing sessions. Chronic pacing adjustment module 1374 coordinates the chronic pacing therapy and the stress augmentation pacing sessions during the transitional periods including the duration for which the acute response to the stress augmentation pacing session is anticipated. In the illustrated embodiment, chronic pacing adjustment module 1374 includes a response timer 1334 and a parameter adjustment module 1336. Response timer 1334 initiates and times a response interval following the stress augmentation pacing session. The response interval includes the anticipated duration of the acute response. In one embodiment, the response interval is pre-programmed based on a duration of the acute response measure for a patient population. In another embodiment, the response interval is programmed to continue while the presence of the acute response is declared by acute response detector 1272. Parameter adjustment module 1336 adjusts the pacing parameters for the chronic pacing therapy during the response interval to allow the patient to benefit from the stress augmentation pacing session whose therapeutic effect is anticipated to continue for a period of time following the session. In one embodiment, in which the acute response includes the vagal surge, parameter adjustment module 1336 adjusts one or more pacing parameters of the chronic pacing therapy to allow the heart to beat at the intrinsic heart rate during the response interval. In a specific embodiment, response time 1334 includes response timer 834, and parameter adjustment module 1336 includes parameter adjustment module 836 as discussed above, which adjusts a pacing rate parameter such as the LRL for a pacing rate lower than the detected intrinsic heart rate by a specified margin during the response interval.

Stress augmentation pacing adjustment module 1370 is an embodiment of stress augmentation pacing adjustment module 1170 and adjusts intermittent cardiac stress augmentation pacing protocol 866 using the acute response signal produced by acute response detector 1272. In one embodiment, stress augmentation pacing adjustment module 1370 approximately optimizes intermittent cardiac stress augmentation pacing protocol 866 using the acute response signal. In various embodiments, stress augmentation pacing adjustment module 1370 adjusts intermittent cardiac stress augmentation pacing protocol 866 using one or more of the one or more parameters each indicative of the level of the acute response, the indication of presence or absence of the acute response, and the duration of the acute response. In the illustrated embodiment, stress augmentation pacing adjustment module 1370 includes a mode selection module 1380, a response assurance module 1382, a session frequency module 1384, and a dose reduction module 1386. In various embodiments, one or more of mode selection module 1380, response assurance module 1382, session frequency module 1384, and dose reduction module 1386 are selectively activated for adjusting intermittent cardiac stress augmentation pacing protocol 866. In various other embodiments, stress augmentation pacing adjustment module 1370 includes any one or more of mode selection module 1380, response assurance module 1382, session frequency module 1384, and dose reduction module 1386.

Mode selection module 1380 selects a stress augmentation pacing mode from a plurality of stress augmentation pacing modes using the acute response signals produced for stress augmentation pacing sessions each associated with a mode of the plurality of stress augmentation pacing modes. For example, intermittent cardiac stress augmentation pacing protocol 866 specifies two or more stress augmentation pacing sessions each using a different stress augmentation pacing mode. The acute responses of the patient to the stress augmentation pacing sessions (i.e., different modes) are detected. The acute response signals each include the one or more parameters associated with a stress augmentation pacing mode of the plurality of stress augmentation pacing modes. Mode selection module 1380 selects the stress augmentation pacing mode associated with the highest level of the acute response as indicated by the acute response signals, and adjusts intermittent cardiac stress augmentation pacing protocol 866 such that the selected stress augmentation pacing mode is specified for the subsequent stress augmentation sessions. In one embodiment, the plurality of stress augmentation pacing modes includes an overdrive mode and a short AV delay mode. The overdrive mode is a pacing mode with a pacing rate substantially higher than the patient's intrinsic heart rate, such as a bradycardia pacing mode, a CRT pacing mode, or an asynchronous pacing mode with pacing parameters programmed for the pacing rate to be higher than the measured intrinsic heart rate by a specified margin. The short AV delay mode is an atrial tracking pacing mode with an AV delay that is substantially shorter than the patient's intrinsic AV conduction interval, such as a bradycardia pacing mode or a CRT pacing mode with the AV delay programmed to be shorter than the measured intrinsic AV conduction interval by a specified margin.

Response assurance module 1382 adjusts parameters of intermittent cardiac stress augmentation pacing protocol 866 in response to the acute response signal indicating the absence of the acute response. In one embodiment, response assurance module 1382 adjusts one or more parameters of intermittent cardiac stress augmentation pacing protocol 866 to increase one or more of a degree and a duration of the cardiac stress augmentation in response to the acute response signal indicating the absence of the acute response. This includes, for example, one or more of increasing the pacing rate in the overdrive mode or decreasing the AV delay in the short AV delay mode, increasing the second pacing period (or the pacing period), increasing the number of cycles (N), and increasing the session frequency. In one embodiment, response assurance module 1382 changes the stress augmentation pacing mode specified in intermittent cardiac stress augmentation pacing protocol 866 in response to the acute response signal indicating the absence of the acute response. This includes, for example, switching from the overdrive mode to the short AV delay mode, or vice versa. In one embodiment, response assurance module 1382 changes one or more timing parameters of intermittent cardiac stress augmentation pacing protocol 866 in response to the acute response signal indicating the absence of the acute response. This includes, for example, changing time of day for delivering each of the stress augmentation pacing sessions, such as changing from delivering the stress augmentation pacing sessions during daytime to delivering the stress augmentation pacing sessions at nighttime, and/or changing a ratio of the non-pacing period to pacing period (or a ratio of the first pacing period to the second pacing period). In one embodiment, response assurance module 1382 suspends the execution of intermittent cardiac stress augmentation pacing protocol 866 for a specified period in response to the acute response signal indicating the absence of the acute response. In one embodiment, the specified period is programmable by the physician or other caregiver. In various embodiments, these functions of response assurance module 1382 are performed with any combination and timing selected by the physician or other caregiver. In one embodiment, response assurance module 1382 suspends the execution of intermittent cardiac stress augmentation pacing protocol 866 when the absence of the acute response remains declared after performing any and all of the other adjustments.

Session frequency module 1384 adjusts the session frequency specified in intermittent cardiac stress augmentation pacing protocol 866 based on the acute response signal indicating the duration of the acute response. The session frequency is the frequency at which the stress augmentation pacing sessions are delivered. For example, if the duration of acute response exceeds 3 hours, session frequency module 1384 sets the session frequency to 1 session per day. If the duration of acute response does not exceed 3 hours, session frequency module 1384 sets the session frequency to 2 sessions per day. In one embodiment, in which the patient has heart failure, severity of the heart failure is measured by autonomic tone indicated by the one or more parameters produced by parameter producer 1260 and included in the acute response signal. Session frequency module 1384 sets a session frequency based on the severity of heart failure as indicated by the one or more parameters. In one embodiment, acute response detector 1272 detects the severity of heart failure by comparing the one or more parameters to one or more specified thresholds and declares the severity as being low, moderate, and higher, for example. Session frequency module 1384 sets the session frequency to 1 session per day if the severity of heart failure is low and 2 sessions per day if the severity of heart failure is moderate. In one embodiment, session frequency module 1384 recommends the session frequency to the physician or other caregiver through external system 115, and adjusts the session frequency upon acceptance of the recommendation. In another embodiment, session frequency module 1384 adjusts the session frequency and communicates the adjustment to the physician or other caregiver through external system 115.

Dose reduction module 1386 reduces one or more of a level and a duration of the cardiac stress augmentation by adjusting parameters of intermittent cardiac stress augmentation pacing protocol 866 using the acute response signal. In one embodiment, dose reduction module 1386 approximately minimizes the level and/or the duration of the cardiac stress augmentation using the acute response signal indicating one or more of the one or more parameters each indicative of the level of the acute response, the presence or absence of the acute response, and the duration of the acute response. In various embodiments, dose reduction module 1386 maintains the therapeutic effect of the stress augmentation pacing sessions by maintaining the one or more parameters each indicative of the level of the acute response above one or more threshold values, maintaining the presence of the acute response, and/or maintaining a specified duration of the acute response. While the therapeutic effect is maintained, dose reduction module 1386 reduces, for example, the number of cycles (N), such as by 1 cycle each time, and/or the second pacing period (the pacing period), such as by 10% each time. In general, dose reduction module 1386 reduces, or approximately minimizes, the amount of pacing pulses delivered to the patient under a stress augmentation pacing mode while ensuring that the patient benefits from such a pacing mode.

Figure 14:
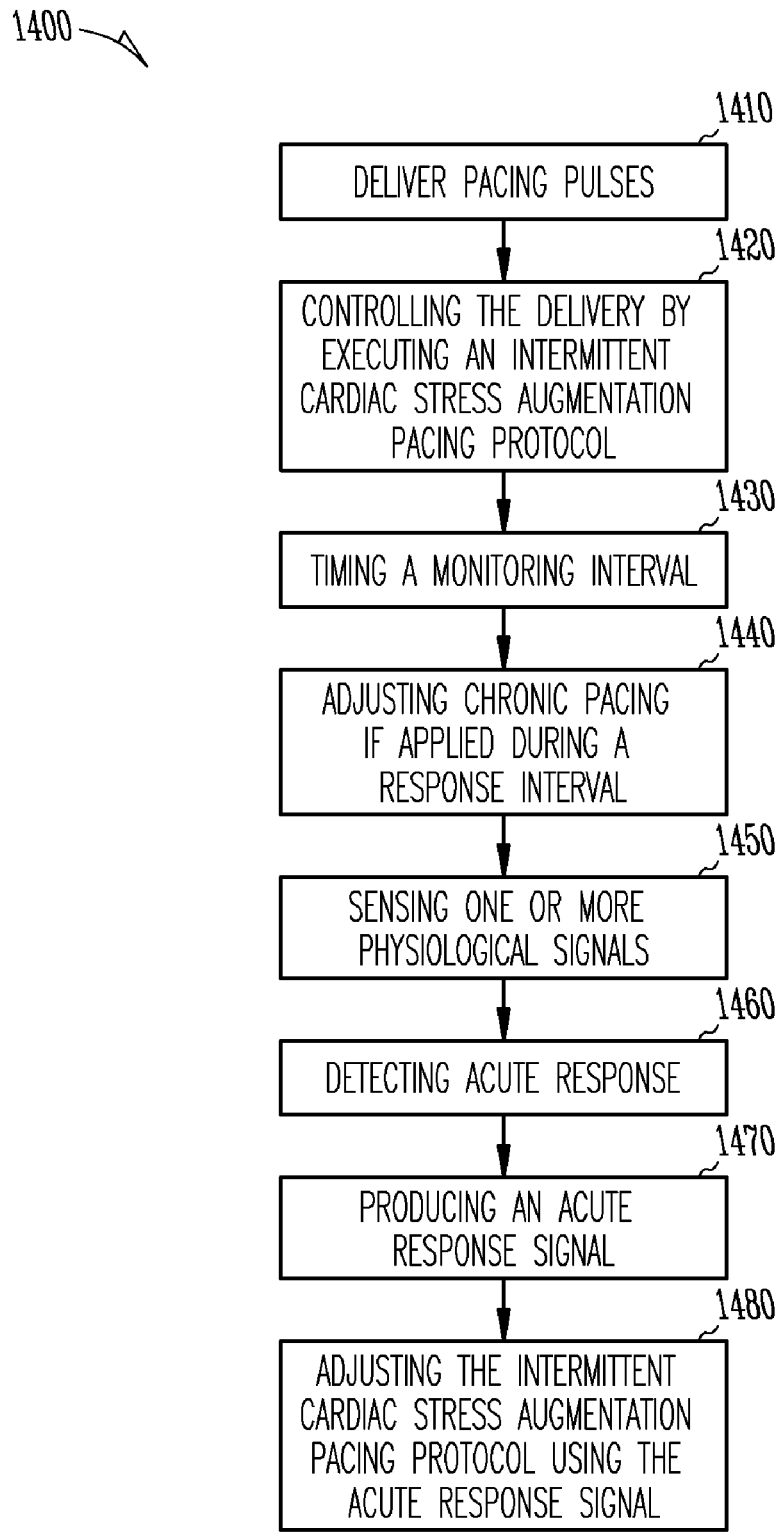
FIG. 14 is a flow chart illustrating an embodiment of a method for adjusting the intermittent cardiac stress augmentation pacing protocol.

FIG. 14 is a flow chart illustrating an embodiment of a method 1400 for adjusting an intermittent cardiac stress augmentation pacing protocol such as intermittent cardiac stress augmentation pacing protocol 866. In one embodiment, method 1400 is performed using system 1120, including the various embodiments of its components as discussed in this document.

At 1410, pacing pulses are delivered to the heart of a patient. At 1420, the delivery of the pacing pulse is controlled by executing the intermittent cardiac stress augmentation pacing protocol. The intermittent cardiac stress augmentation pacing protocol specifies a plurality of stress augmentation pacing sessions and a stress augmentation pacing mode including pacing parameters. The pacing parameters are selected to augment cardiac stress to the level effective in slowing or stopping progression of a cardiac disorder.

At 1430, a monitoring interval is timed. The monitoring interval includes an anticipated duration of an acute response to a stress augmentation pacing session of the plurality of stress augmentation pacing sessions. In one embodiment, the acute response includes vagal surge resulting from the stress augmentation pacing session.

At 1440, if the patient receives a chronic pacing therapy that is suspended during each of the stress augmentation pacing sessions and resumed upon completion of the session while the acute response is still present, the chronic pacing therapy is adjusted so as not to suppress the therapeutic benefit of the stress augmentation pacing session to the patient. In one embodiment, a response interval is initiated and timed following each of the stress augmentation pacing sessions. The response interval includes the anticipated duration of the acute response. In one embodiment, in which the acute response includes the vagal surge, one or more pacing parameters of the chronic pacing therapy are adjusted to allow the heart to beat at the intrinsic heart rate during the response interval. For example, the LRL of the chronic pacing therapy mode is lowered to a rate lower than the detected intrinsic heart rate by a specified margin during the response interval.

At 1450, one or more physiological signals are sensed. The one or more physiological signals are each indicative of a level of the acute response. In one embodiment, the one or more physiological signals includes one or more physiological signals each indicative of a level of the vagal surge. In a specific embodiment, the one or more physiological signals each indicative of the level of the vagal surge include at least a cardiac signal. In various embodiments, the one or more physiological signals include one or more cardiac signals indicative of cardiac depolarizations, a signal indicative of respiration, a PAP signal, a signal indicative of heart sounds, and any signals indicative of the vagal surge and/or cardiac contractility.

At 1460, the acute response is detected using the one or more physiological signals sensed during the monitoring interval. At 1470, an acute response signal is produced after expiration of the monitoring interval. The acute response signal is indicative of a status of the acute response to the stress augmentation pacing session. The detection of the acute response includes producing one or more parameters each indicative of a level of the acute response using the sensed one or more physiological signals. In one embodiment, in which the acute response includes the vagal surge, the one or more parameters include at least an intrinsic heart rate. In various embodiments, the one or more physiological signals include one or more of the intrinsic heart rate, AV interval, short-term HRV, minute ventilation, PAP, dPAP/dt, heart sound parameter, and other parameters suitable for indicating vagal surge and/or cardiac contractility. In one embodiment, the acute response is detected by comparing the one or more parameters to one or more thresholds, and an absence or presence of the acute response is declared using an outcome of the comparison. In one embodiment, a duration of the acute response is detected as a time interval during which the presence of the acute response is declared. In various embodiments, the acute response signal includes the one or more parameters each indicative of the level of the acute response, indication of the presence or absence of the acute response, and/or the duration of the acute response.

At 1480, the intermittent cardiac stress augmentation pacing protocol is adjusted using the acute response signal. In one embodiment, parameters of the intermittent cardiac stress augmentation pacing protocol are approximately optimized using the acute response signal. In various embodiments, the intermittent cardiac stress augmentation pacing protocol is adjusted by one or more of selecting a stress augmentation pacing mode, adjusting parameters in response to the absence of the acute response, setting the session frequency, and reducing the dose of the stress augmentation pacing.

In one embodiment, a stress augmentation pacing mode is selected from a plurality of stress augmentation pacing modes using the acute response signals produced for stress augmentation pacing sessions each associated with a mode of the plurality of stress augmentation pacing modes. The acute response signals each include the one or more parameters associated with a stress augmentation pacing mode of the plurality of stress augmentation pacing modes. The stress augmentation pacing mode associated with the highest level of the acute response is selected for use in the subsequent stress augmentation pacing sessions. Examples of the stress augmentation pacing modes include the overdrive mode and the short AV delay mode.

In one embodiment, parameters of the intermittent cardiac stress augmentation pacing protocol are adjusted in response to the acute response signal indicating the absence of the acute response, as further discussed below with reference to FIG. 15.

In one embodiment, the session frequency specified in the intermittent cardiac stress augmentation pacing protocol is set based on the acute response signal indicating the duration of the acute response. For example, if the duration of acute response exceeds a specified threshold duration, a lower session frequency is set; otherwise, a higher session frequency is set. In one embodiment, one or more parameters indicative of autonomic tone are produced to be used as a measure of severity of heart failure. The session frequency is set based on the severity of heart failure as indicated by the one or more parameters. For example, if the severity of heart failure is low, a lower session frequency is set. If the severity of heart failure is moderate, a higher session frequency is set. In one embodiment, the session frequency is recommended to the physician or other caregiver and applied in the subsequent stress augmentation pacing sessions only upon acceptance by the physician or other caregiver.

In one embodiment, one or more of a level and a duration of the cardiac stress augmentation as specified by parameters of the intermittent cardiac stress augmentation pacing protocol is reduced using the acute response signal. In one embodiment, one or more of the level and the duration of the cardiac stress augmentation are approximately minimized. This is to minimize the amount of unnecessary augmentation of the cardiac stress in the patient. In various embodiments, the parameters are adjusted for maintaining the acute response by using the acute response signal, such as by maintaining a specified level of the acute response by comparing the one or more parameters to one or more threshold values, maintaining the presence of the acute response, and maintaining a specified duration of the acute response. While the level and/or the duration of the acute response are maintained, the number of cycles (N) and/or the second pacing period (the pacing period) are reduced to reduce the amount of pacing pulses delivered under the stress augmentation pacing mode.

FIG. 15 is a flow chart illustrating an embodiment of a method 1500 for adjusting the intermittent cardiac stress augmentation pacing protocol in response to the acute response signal indicating the absence of the acute response. At each of 1510A-D, the acute response to a stress augmentation session is detected and the acute response signal for that stress augmentation session is produced. The acute response signal indicates the absence or presence of the acute response for the stress augmentation session. At each of 1512A-D, if the acute response signal indicates the absence of the acute response for the stress augmentation session, an adjustment of the intermittent cardiac stress augmentation pacing protocol is performed, or the execution of the intermittent cardiac stress augmentation pacing protocol is suspended. If the acute response signal indicates the presence of the acute response for the stress augmentation session, no further adjustment is necessary, and performance of method 1500 is completed at 1560. In various embodiments, the selection and/or order of adjustments at 1520, 1530, and 1540 are programmable by the physician or other caregiver, while the illustrated embodiment provides an example.

At 1520, parameters of the intermittent cardiac stress augmentation pacing protocol are adjusted to increase one or more of a degree and a duration of the cardiac stress augmentation as indicated by the acute response signal. This includes, for example, one or more of increasing the pacing rate in the overdrive mode or decreasing the AV delay in the short AV delay mode, increasing the second pacing period (or the pacing period), increasing the number of cycles (N), and increasing the session frequency.

At 1530, the stress augmentation pacing mode specified in the intermittent cardiac stress augmentation pacing protocol is changed. This includes, for example, switching between the overdrive mode and the short AV delay mode.

At 1540, timing parameters of the intermittent cardiac stress augmentation pacing protocol are adjusted. This includes, for example, changing time of day for each stress augmentation pacing session (such as switching between delivering during daytime and delivering during nighttime) or changing a ratio of the pacing period to non-pacing period.

At 1550, the execution of the intermittent cardiac stress augmentation pacing protocol is suspended for a specified period. In one embodiment, the specified period is programmable by the physician or other caregiver. In one embodiment, the execution of the intermittent cardiac stress augmentation pacing protocol is suspended only after all the parameter adjustments, such as those at 1520, 1530, and 1540, fail to restore the presence of the acute response.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for pacing a heart, comprising:
   a monitoring circuit including:
   a monitoring timer configured to initiate and time a monitoring interval including an anticipated duration of vagal surge resulting from a delivery of a first therapy;
   a sensing circuit configured to sense one or more physiological signals each indicative of a level of the vagal surge, the one or more physiological signals including at least a cardiac signal; and
   a detection circuit configured to detect one or more parameters each indicative of the level of the vagal surge using the sensed one or more physiological signals, the one or more parameters including at least an intrinsic heart rate;
   a pacing output circuit configured to deliver a second therapy including delivering pacing pulses, the second therapy different from the first therapy; and
   a pacing control circuit coupled to the monitoring circuit and the pacing output circuit, the pacing control circuit configured to control the delivery of the second therapy using pacing parameters and including:
   a response timer configured to initiate and time a response interval following the delivery of the first therapy, the response interval including the anticipated duration of the vagal surge; and
   a parameter adjustment module configured to adjust one or more pacing parameters of the pacing parameters to allow the heart to beat at the intrinsic heart rate during the response interval.

2. The system of claim 1, wherein the response timer is configured to initiate the response interval upon expiration of a delay interval starting at an end of the delivery of the first therapy, and the parameter adjustment module is configured to lower a lower rate limit (LRL) of the pacing parameters by a specified margin below the detected intrinsic heart rate during the response interval.

3. The system of claim 1, comprising a therapy device configured to perform delivery of the first therapy, and wherein the monitoring timer is configured to initiate the monitoring interval in response to the delivery of the first therapy.

4. The system of claim 3, wherein the response timer is configured to initiate the response interval upon expiration of a delay interval starting at an end of the delivery of the first therapy.

5. The system of claim 3, comprising:
   a first implantable medical device including the monitoring circuit, the pacing circuit, and the pacing control circuit; and
   a second implantable or non-implantable medical device including the therapy device.

6. The system of claim 3, comprising an implantable medical device including the monitoring circuit, the pacing circuit, the pacing control circuit, and the therapy device.

7. The system of claim 6, wherein the therapy device is configured to deliver a neurostimulation therapy.

8. The system of claim 6, wherein the therapy device comprises the pacing circuit and the pacing control circuit, and the pacing control circuit comprises:
   a memory circuit;
   an intermittent cardiac stress augmentation pacing protocol stored in the memory circuit, the intermittent cardiac stress augmentation pacing protocol specifying stress augmentation pacing sessions each being the first therapy and including alternating non-pacing and pacing periods, the non-pacing periods each having a non-pacing duration during which no pacing pulse is timed to be delivered, the pacing periods each having a specified pacing duration during which a plurality of the pacing pulses is timed to be delivered using pacing parameters selected to augment cardiac stress to the level effective in slowing or stopping progression of the cardiac disorder; and
   a pacing protocol execution module configured to control the delivery of the pacing pulses by executing the intermittent cardiac stress augmentation pacing protocol.

9. The system of claim 6, wherein the detection circuit is configured to produce a pre-event value of each of the one or more parameters before the delivery of the first therapy, a post-event value of the each of the one or more parameters after the delivery of the first therapy during the monitoring interval, and a change value of each of the one or more parameters, the change value being a difference between the post-event value and the pre-event value of the each of the one or more parameters.

10. The system of claim 9, wherein the sensing circuit is configured to sense the cardiac signal and one or more of a signal indicative of respiration, a pulmonary artery pressure (PAP) signal, and a signal indicative of heart sounds, and the detection circuit is configured to detect the intrinsic heart rate and one or more of an atrioventricular (AV) interval, a short-term heart rate variability (HRV) indicative of heart rate turbulence (HRT), a minute ventilation, a PAP, or rate of change in the PAP (dPAP/dt), and a heart sound parameter.

11. The system of claim 1, wherein the pacing output circuit is configured to deliver the first therapy and the second therapy, the first therapy being a temporary pacing therapy, the second therapy being a chronic pacing therapy, and the pacing control circuit is configured to control the delivery of the first therapy and the delivery of the second therapy.

12. The system of claim 11, comprising an implantable medical device including the monitoring circuit, the pacing output circuit, and the pacing control circuit.

13. The system of claim 1, further comprising a therapy device configured to deliver a neurostimulation therapy as the first therapy.

14. The system of claim 13, comprising an implantable medical device including the monitoring circuit, the pacing output circuit, the pacing control circuit, and the therapy device.

15. The system of claim 1, wherein the monitoring timer is configured to initiate and time the monitoring interval being an interval programmable between approximately 2 and 3 hours.

16. The system of claim 15, wherein the response timer is configured to initiate the response interval in response to an end of the delivery of the first therapy.

17. The system of claim 16, wherein the response timer is configured to initiate and time the response interval being another interval programmable between approximately 2 and 3 hours.

18. The system of claim 17, wherein the response timer is configured to initiate the response interval upon expiration of a delay starting at the end of the delivery of the first therapy and programmable between approximately 0 and 10 minutes.

19. The system of claim 1, wherein the response timer is configured to terminate the response interval before a termination of the monitoring interval.

20. The system of claim 1, wherein the response timer is configured to terminate the response interval at a termination of the monitoring interval.

21. A method for operating a system for pacing a heart, comprising:
delivering a first therapy;
sensing a cardiac signal from the heart;
delivering a second therapy including delivery of pacing pulses to the heart, the second therapy different from the first therapy;
controlling the delivery of the second therapy using pacing parameters;
initiating a monitoring interval in response to the delivery of the first therapy, the monitoring interval including an anticipated duration of vagal surge resulting from the delivery of the first therapy;
detecting an intrinsic heart rate from the cardiac signal during the monitoring interval;
initiating a response interval in response to the delivery of the first therapy, the response interval including the anticipated duration of the vagal surge; and
adjusting one or more pacing parameters of the pacing parameters to allow the heart to beat at the intrinsic heart rate during the response interval.

22. The method of claim 21, wherein initiating the monitoring interval comprises initiating the monitoring interval in response to the delivery of the first therapy.

23. The method of claim 22, comprising programming the monitoring interval and the response time to terminate simultaneously at approximately 2 to 3 hours following an end of the delivery of the first therapy.

24. The method of claim 22, wherein initiating the response interval comprises initiating the response interval upon expiration of a delay interval starting at an end of the delivery of the first therapy, and comprising programming the delay interval to a time interval between approximately 0 and 10 minutes.

25. The method of claim 21, comprising:
sensing the cardiac signal and one or more additional physiological signals each indicative of a level of the vagal surge; and
detecting the intrinsic heart rate and one or more additional parameters each indicative of the level of the vagal surge.

26. The method of claim 21, comprising producing a pre-event value of the intrinsic heart rate before the delivery of the first therapy, a post-event value of the intrinsic heart rate after the delivery of the first therapy during the monitoring interval, and a change value of the intrinsic heart rate, the change value being a difference between the post-event value and the pre-event value.

27. The method of claim 21, wherein adjusting the one or more pacing parameters comprises lowering a lower rate limit (LRL) to a value below the detected intrinsic heart rate by a specified margin during the response interval if the lowered LRL exceeds a specified minimum.

28. The method of claim 27, wherein lowering the LRL comprises lowering the LRL to a value below the detected intrinsic heart rate by approximately 15 beats per minute.

29. The method of claim 21, comprising delivering an intermittent cardiac stress augmentation pacing therapy including stress augmentation pacing sessions each being the first therapy and including alternating non-pacing and pacing periods, the non-pacing periods each having a non-pacing duration during which no pacing pulse is timed to be delivered, the pacing periods each having a specified pacing duration during which a plurality of the pacing pulses is timed to be delivered using pacing parameters selected to augment cardiac stress to the level effective in slowing or stopping progression of a cardiac disorder.

30. The method of claim 21, comprising delivering an intermittent cardiac stress augmentation pacing therapy including stress augmentation pacing sessions each being the first therapy and including alternating first and second pacing periods, the first pacing periods each having a first pacing duration during which a plurality of the pacing pulses is timed to be delivered according to a first pacing mode, the second pacing periods each having a second pacing duration during which a plurality of the pacing pulses is timed to be delivered according to a second pacing mode including pacing parameters selected to augment cardiac stress to the level effective in slowing or stopping progression of a cardiac disorder.

31. The method of claim 21, wherein the first therapy is a temporary pacing therapy, and the second therapy is a chronic pacing therapy.

32. The method of claim 31, wherein delivering the first therapy comprises delivering the first therapy from an implantable medical device, and delivering the second therapy comprises delivering the second therapy from the implantable medical device.

33. The method of claim 21, wherein delivering the first therapy comprises delivering a neurostimulation therapy.

34. The method of claim 33, wherein delivering the first therapy comprises delivering the first therapy from a non-implantable medical device, and delivering the second therapy comprises delivering the second therapy from an implantable medical device.

35. The method of claim 33, wherein delivering the first therapy comprises delivering the first therapy from a first implantable medical device, and delivering the second therapy comprises delivering the second therapy from a second implantable medical device.

36. The method of claim 21, wherein delivering the first therapy comprises delivering a drug therapy.

37. The method of claim 21, wherein delivering the first therapy comprises delivering a therapy that enhances cardiac contractility.

38. The method of claim 25, wherein sensing the one or more additional physiological signals comprises sensing a respiration signal.

39. The method of claim 25, wherein sensing the one or more additional physiological signals comprises sensing a pulmonary artery pressure signal.

40. The method of claim 25, wherein sensing the one or more additional physiological signals comprises sensing a heart sound signal.

* * * * *